United States Patent [19]
Newton et al.

[11] Patent Number: 5,312,401

[45] Date of Patent: May 17, 1994

[54] ELECTROSURGICAL APPARATUS FOR LAPAROSCOPIC AND LIKE PROCEDURES

[75] Inventors: David W. Newton, Boulder; Roger C. Odell, Louisville; Don R. Boyle, Boulder, all of Colo.

[73] Assignee: Electroscope, Inc., Boulder, Colo.

[21] Appl. No.: 727,946

[22] Filed: Jul. 10, 1991

[51] Int. Cl.$^5$ .............................................. A61B 17/39
[52] U.S. Cl. ......................................... 606/46; 606/35; 606/42
[58] Field of Search .......................... 606/32–35, 606/37–42, 44–47

[56] References Cited

U.S. PATENT DOCUMENTS

| | | | |
|---|---|---|---|
| 3,707,149 | 12/1972 | Hao et al. | 606/37 |
| 3,933,157 | 0/1976 | Bjurwill et al. | 606/35 |
| 4,184,492 | 0/1980 | Meinke et al. | 606/46 |
| 4,200,104 | 4/1980 | Harris | 606/35 |
| 4,494,541 | 1/1985 | Archibald | 606/32 |
| 4,615,330 | 10/1986 | Nagasaki et l. | 606/42 |
| 4,617,927 | 10/1986 | Manes | 606/38 |
| 4,844,063 | 7/1989 | Clark | 606/37 |
| 5,087,257 | 2/1992 | Farin et al. | 606/35 |

FOREIGN PATENT DOCUMENTS 3013784 10/1890 Fed. Rep. of Germany ........ 606/46
1139927 of 1961 Fed. Rep. of Germany .

Primary Examiner—David M. Shay
Attorney, Agent, or Firm—Sixbey, Friedman, Leedom & Ferguson

[57] ABSTRACT

A safety shield for use in laparoscopic or like electrosurgical procedures where the shield surrounds the active electrode and extends from a trocar or the like to the field of view of the surgical procedure. The shield is connected to the return lead via a low impedance path which includes monitor circuitry for determining whether the shield current is associated with an abnormal condition.

42 Claims, 11 Drawing Sheets

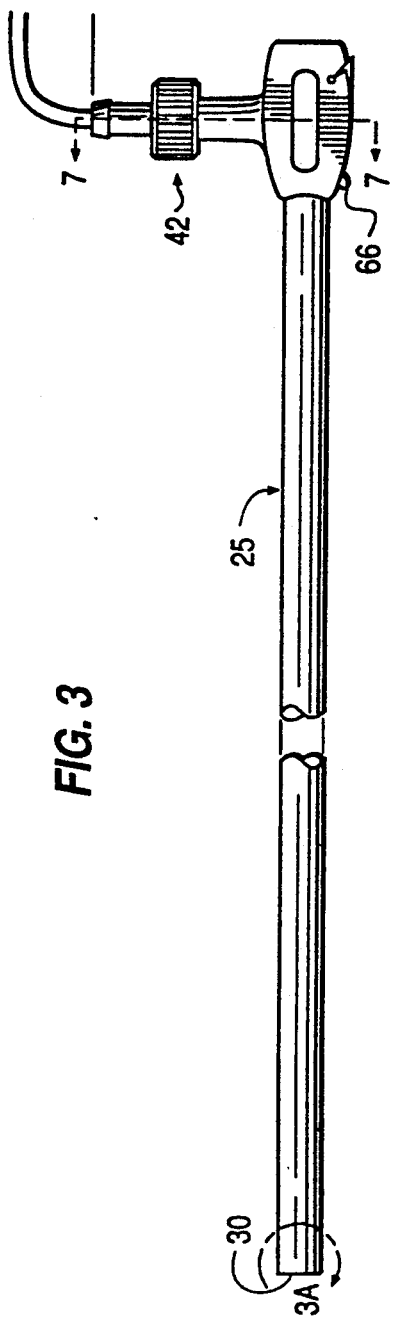
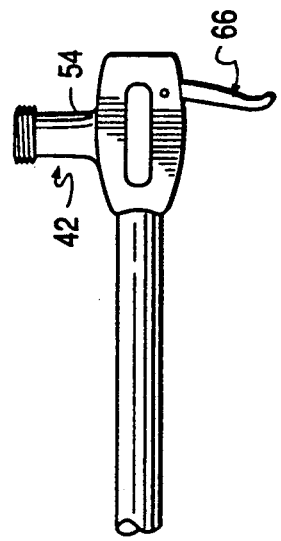
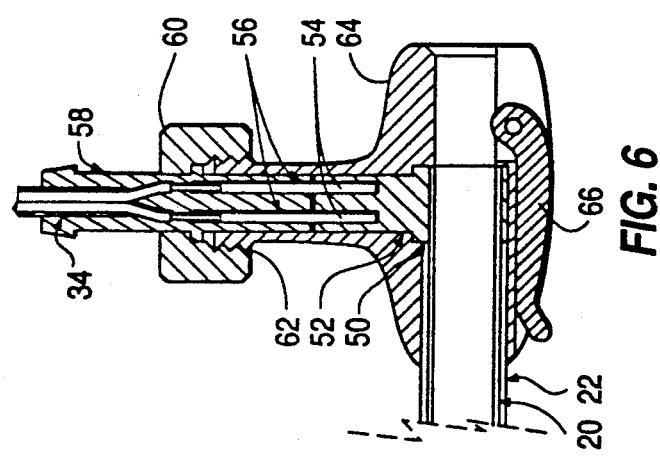
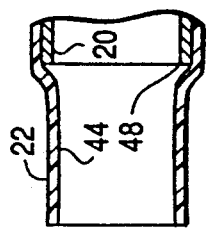
FIG. 3
FIG. 3A
FIG. 5
FIG. 6

ELECTROSURGICAL APPARATUS FOR LAPAROSCOPIC AND LIKE PROCEDURES

BACKGROUND OF THE INVENTION

This invention is related to electrosurgical apparatus and in particular to such apparatus for performing laparoscopic, pelviscopic, athroscopic, thoroscopic and like procedures.

Procedures of the foregoing type are experiencing explosive growth in that incisions are kept to a minimum size and thus such procedures facilitate shorter hospital stays and lower costs. For example, with laparoscopic surgery, a patient can return to normal activity within about one week, whereas with procedures where a large incision is made, about a month for full recovery may be required.

It is to be understood that hereinafter and in the claims, whenever the term "laparoscopic" is employed, similar procedures such as pelviscopic, arthroscopic, thoroscopic, and the like where small incisions of the foregoing type are made are also encompassed by this term.

Referring to FIG. 1, there is illustrated a prior art electrosurgical laparoscopic apparatus including a trocar sheath or cannula 10 which is conventionally used to provide a conduit through a patient's skin into the peritoneal cavity. Removably insertable through the trocar sheath is an active electrode probe 12 which includes an electrode 14 and an insulative coating 16 thereon. The tip 18 of the probe may be of different conventional shapes such as needle-shape, hook-shape, spatula-shape, graspers, scissors, etc. and serve various conventional functions such as suction, coagulation, irrigation, pressurized gas, cutting, etc. There are various problems which may arise with respect to the use of the prior art apparatus when used in laparoscopic or like procedures.

A first problem may arise if the insulation 16 on the active electrode is damaged thereby allowing the active current (possibly in the form of arcing) to pass therethrough directly to the patient's tissue (possibly the bowel or colon) whereby peritonitis may set in within several days. The arcing may occur out of the surgeon's field of view which may extend as little as about 2 centimeters from the tip of the active electrode (or the surgical field). The field of view is typically established by illumination and viewing sources inserted through one or more other trocar sheaths at other incisions.

Out of the field of view, there can be many centimeters of insulated active electrode which extend between the trocar sheath and the field of view. This area which is out of the field of view is potentially dangerous. Here, the insulated active electrode may come into contact with the bowel in procedures where the gall bladder, for example, is removed. If the damaged insulation and thus the attendant arcing were to occur within the field of view, the surgeon normally would immediately observe this and deactivate the generator. However, the damaged insulation can and more probably will occur at a site removed from the field of view and thus the surgeon will not be able to observe the arcing which is occurring at the bowel. Furthermore, due to the repeated insertion of the active electrode probe through the trocar sheath, the insulation thereon can be damaged especially since this accessory is quite often pushed through the trocar sheath rather roughly. Hence, damage to the active electrode insulation is particularly a problem in that the full active current may pass through the area of damaged insulation to the return electrode via an unintended site such as the bowel.

A second problem which can arise with the prior art device of FIG. 1 is caused by a capacitive effect where one electrode of the capacitance is the active electrode and the other electrode of the capacitance is the metallic trocar sheath and the dielectric between these elements is the insulation on the active electrode, as can be seen in FIG. 1. Current from the active electrode will be capacitively coupled to the trocar sheath and then returned through the body and the return electrode to the generator. If this current becomes concentrated, for example, between the trocar sheath and an organ such as the bowel, the capacitive current can cause a burn to the organ.

A third potential problem occurs if the active electrode contacts another instrument within the peritoneal cavity such as metallic grippers or the like. The above-mentioned capacitive effect also arises in this situation where the first electrode is the active electrode and the second electrode is the metallic graspers or the like. Thus, where the grippers contact a unintended site, injury may occur.

SUMMARY OF THE INVENTION AND DISCUSSION OF PRIOR ART

To render laparoscopic electrosurgical procedures more safe and thus overcome the above-mentioned problems, the present invention provides a tubular, insulated, conductive safety shield which extends at least from the trocar sheath to the field of view (that is, typically within less than two centimeters from the active electrode tip). This provides the protection which is needed with respect to the above-discussed first problem where arcing may occur at an unintended site out of the field of view. In particular, the insulated shield may be first inserted through the trocar sheath and then the active electrode inserted through the insulated shield although the order is not important. Thus, the active electrode may be assembled to the shield before insertion of the shield and active electrode through the trocar sheath.

The insulation is provided at least on the outer surface of the shield and is preferably also provided on the inner surface of the shield. The purpose of the insulation on the outer surface is to insure that the shield is insulated from the trocar sheath and to prevent the shield from becoming an unintended return electrode. One purpose of the insulation at the inner surface of the shield is to provide an additional layer of insulation if the insulation on the active electrode fails.

Assuming the insulation on the active electrode is damaged, current will pass through the damaged insulation to the shield and then be returned to the return lead via a low impedance electrical connection between the shield and the return lead of the electrosurgical generator where the impedance should be less than about 20 ohms. A monitor circuit responsive to the shield current preferably deactivates the electrosurgical generator whenever the shield current corresponds to an abnormal condition such as an insulation breakdown.

The insulated shield of the present invention also addresses the second and third above-mentioned problems by harmlessly returning any current which is capacitively coupled to the shield to the return lead via the above-mentioned low impedance connection.

U.S. Pat. No. 4,184,492 to H. Meinke et al. discloses an electrosurgical resectoscope wherein insulation may be provided on the outer surface of an instrument body and where the instrument body may be connected to the return lead via a monitor circuit. However, this apparatus is not concerned with providing protection between the instrument body and the field of view. Furthermore, there is no suggestion of a safety shield in Meinke et al. and, in particular, a safety shield which extends between a trocar sheath and the field of view. Moreover, the Meinke et al resectoscope is prone to undesired capacitive coupling to other instruments. Moreover, the monitor circuit of Meinke et al. is not sensitive to spectral components or phase aspects of the sensed current in a trocar sheath whereas such parameters of the sensed shield current are important in the present invention with respect to the detection of active electrode insulation breakdown, as will be described in more detail hereinafter.

The monitoring circuitry of the present invention may be integral with the electrosurgical generator or may be separate from it and attached as an outboard module. In general, the safety shields of the present invention may be used in laparoscopic, pelvoscopic, arthroscopic, thoroscopic, and other procedures where punctures are made in the patient's skin. The shields may be part of an active accessory or they may be separate and used over existing accessories. The accessories are intended for use with insulating or conductive trocar sheaths which form a conduit through the skin.

As stated above, insulation is provided at least on the outer surface of the shield principally to prevent the shield from becoming a parallel return electrode. The shield may also have redundant internal insulation to add to the accessory insulation. Moreover, the insulation at the shield tip is designed to prevent surface conduction from the active electrode to the shield tip.

The monitor circuitry may evaluate various parameters of the shield current to determine whether an abnormal condition such as active electrode insulation breakdown has occurred. Thus, the phase of the active current or voltage may be measured with respect to that of the shield current or voltage. Alternatively, or in addition to, a predetermined spectral content of the shield current may be analyzed. Further, relative amplitudes of the sensed shield current and the generator return current may be compared whereby a threshold ratio may be defined which indicates a hazard. Moreover, the shield current may be compared with an absolute limit to provide a fault condition indication.

Furthermore, the outputs of the measurements described above may be combined so that individual measurement results not sufficient to produce an alert may be evaluated together to produce such an alert.

Moreover, the connection of the shield is redundant and monitored by providing a small sensing current through the pair of conductors connected to the shield. If the circuit to and from the shield is not complete, a fault condition is sensed.

The results of the measurements of shield current flow may be presented in digital or analog form. These results may then be recorded on a computer or chart recorder for future reference.

The safety shield may also be used with hand pieces used to perform tonsillectomies and the like.

Since any insulation can become damaged, a disposable (limited use) shield with a complete insulation system may also be used with uninsulated instruments so that all insulation is replaced with each use. This embodiment enhances cleanability since the reusable instrument has little, if any, interface with the insulation.

Means may also be provided to adjustably position the tip of the active probe as desired by the user with respect to the distal end of the shield and then latch the active probe in place at the desired position. The adjustability feature is advantageous for several reasons including providing a capability whereby the tip exposure can be adjustably limited.

Means may further be provided to prevent the shield from becoming a return electrode by requiring the use of a dual-area return electrode. Thus, the monitor may employ an industry standard connector, which is used to monitor return electrodes. This connector uses a pin to designate a dual area electrode and the monitor of the present invention may have a switch activated by that pin. A fault condition is presented if use is attempted without the dual-area return electrode as represented by the pin. Moreover, by providing insulation on the inner and outer surfaces of the shield, this also prevents the shield from becoming a return electrode.

In another embodiment of the invention, a tubular insulative member is removably insertable through the trocar sheath and includes an elongated port through which irrigation fluid or suction or gas may pass. The active electrode probe is attached to the end of the tubular member where the electrical connection thereto extends through the insulated portion of the tubular member and where a tubular conductive shield surrounding the electrical conductor is also disposed within the insulated portion of the tubular member.

These and other objects of the invention will become apparent from a reading of the following specification and claims taken with the drawings.

BRIEF DESCRIPTION OF THE DRAWINGS

FIG. 3 is a side view of the laparoscopic apparatus of FIG. 2.

FIG. 3A is a cross-sectional view of an enlarged end portion of the apparatus of FIG. 3.

FIG. 5 is a side view of the apparatus of FIG. 3 with the latch thereof in its release position.

FIG. 6 is a cross-sectional view taken along the line 6—6 of FIG. 4 which illustrates in detail an illustrative electrical connector to the shield.

DETAILED DESCRIPTION OF PREFERRED EMBODIMENTS

Figure 1:
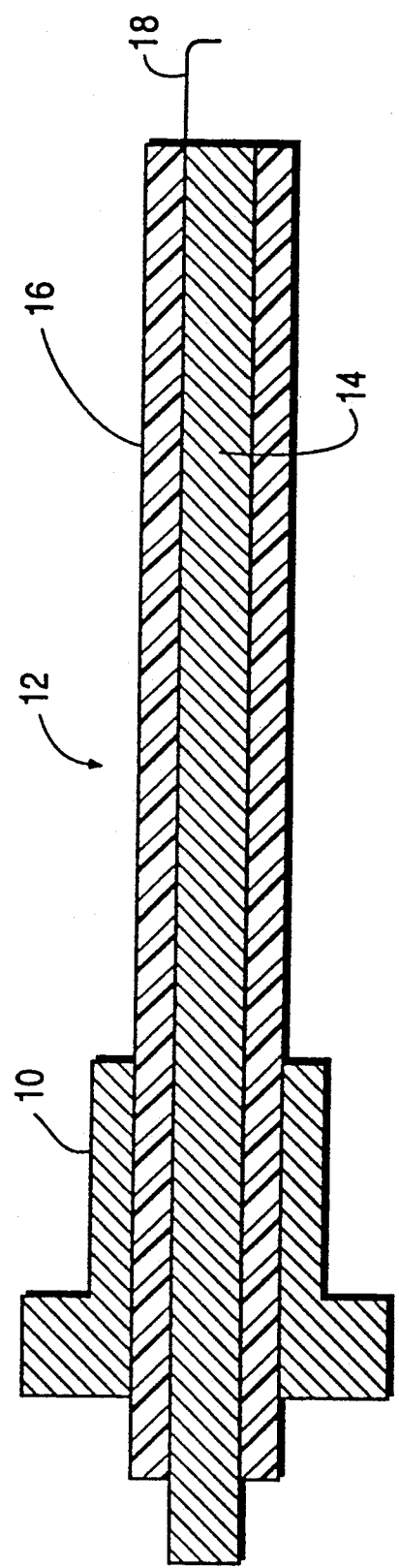
FIG. 1 is a cross-sectional view of a prior art laparoscopic electrosurgical apparatus.
Figure 2:
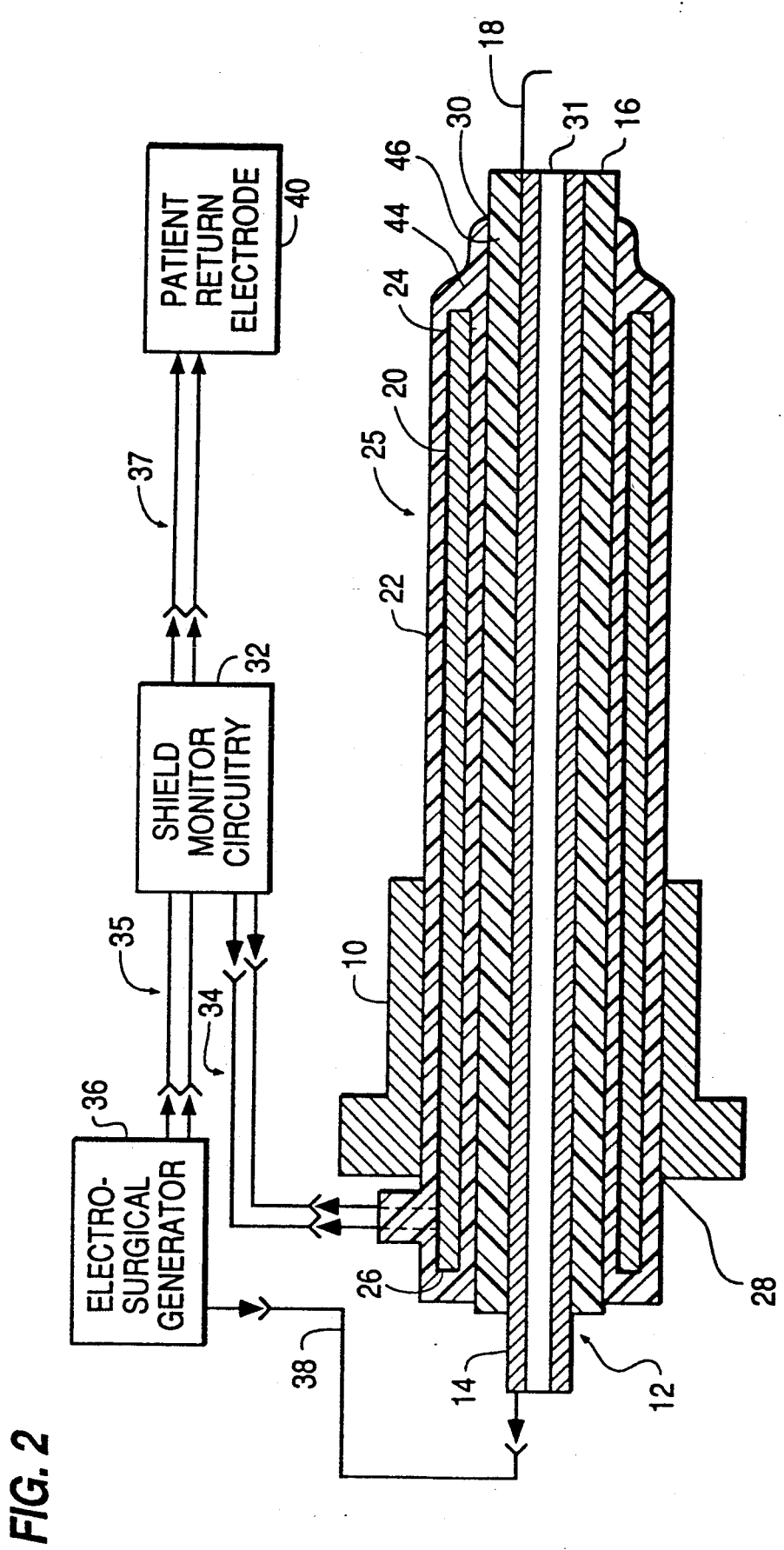
FIG. 2 is a cross-sectional view of an illustrative laparoscopic apparatus in accordance with the present invention.
Figure 4:
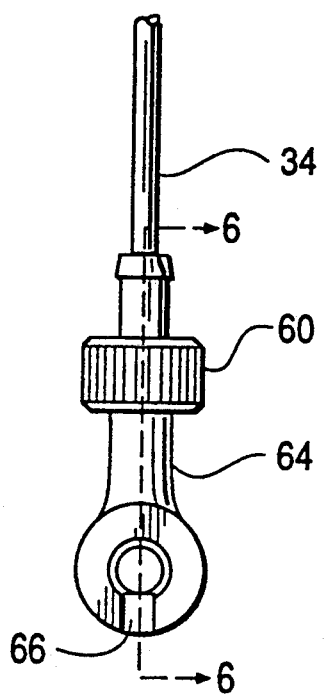
FIG. 4 is an end view of the laparoscopic apparatus of FIG. 3.
Figure 7:
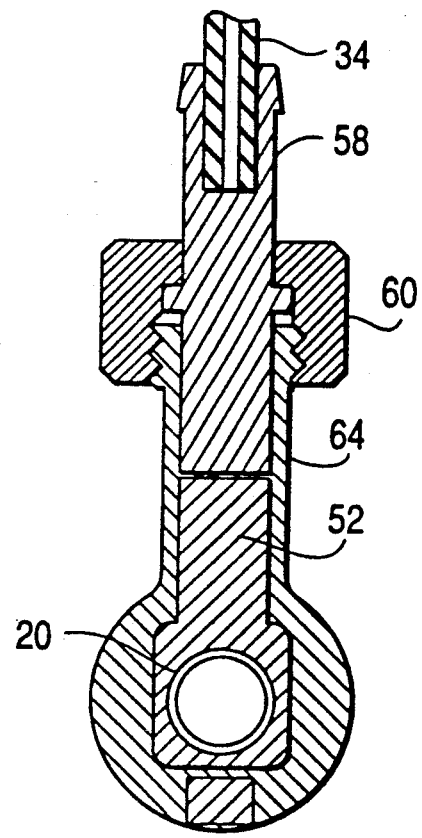
FIG. 7 is a cross-sectional view taken along the line 7—7 of FIG. 3 which further illustrates the electrical connector of FIG. 6.

Referring to the drawing where like reference numerals refer to like parts, there is illustrated in FIG. 2 an illustrative laparoscopic electrosurgical apparatus in accordance with the present invention. A tubular safety shield assembly 25 includes a tubular shield 20 having a layer of insulation 22 provided on the outer surface thereof and an optional layer of insulation 24 provided on the inner surface thereof. The tubular shield assembly is inserted through trocar sheath 10 to thereby provide a passageway through which the active electrode probe 12 may be inserted. An elongated port 31 may extend through the active electrode through which irrigation fluids, suction, a pressurized gas stream, etc. may pass. When active probe 12 and tubular shield assembly 25 are in their respective inserted positions as shown in FIG. 2, the shield 20 surrounds the active probe from at least (a) a proximal point 26 prior to the entry point 28 of the active probe into the trocar sheath 10 to (b) a distal point 30 in proximity to the tip 18 of the active probe.

Shield monitor circuitry 32 is connected to shield 20 via a dual conductor lead 34 whereby the integrity of the connection of the shield to the monitor circuitry can be monitored.

The active electrode probe 12 is connected to an electrosurgical generator 36 which may be of a conventional type via an active lead 38. The electrosurgical generator is connected to a patient return electrode 40, which preferably should be of the dual area type, via the shield monitor circuitry 32 and, in particular, the return terminal of the generator is connected to circuitry 32 via lead 35 while the circuitry 32 is connected to the return electrode via lead 37. As will be described hereinafter, upon detection of a fault condition by the shield monitor circuitry, the electrosurgical generator 36 may be deactivated by opening a relay in the connection between the generator and patient return electrode 40 although other means may also be employed to deactivate the generator.

Referring to FIGS. 3 through 7, there is illustrated the shield assembly 25 including shield connector assembly 42. In the FIG. 3 embodiment, insulation 22 is provided only on the outer surface of shield 20 as can be seen in FIG. 3A, which is an enlarged cross-sectional view of the distal end 30 of the shield assembly 25. Thus, there is no inner insulation layer in FIG. 3A corresponding to inner insulation layer 24 of FIG. 2. The portion 44 of insulating layer 22 extending beyond sleeve 20 is preferably of reduced inner diameter so that when the active electrode probe is inserted through the shield assembly 25, a tight connection will result between the active probe and portion 44 as illustrated in FIG. 2 at 46 and FIG. 3A at 44. Hence, the insulation portion 44 at the shield tip prevents surface conduction from active electrode tip 18 to the distal end 48 of shield 20. The reduced diameter portion 44 may be effected by heat shrinking or other appropriate techniques.

Referring to FIG. 6, the shield tube 20 is press fit at 50 to a connector element 52. Connector 52 has two pin receptacles 54 adapted to receive the pins 56 of a plug 58 attached to dual lead 34 of FIG. 2. The plug 58 is removably secured to connector 52 via a thumb wheel 60 threaded onto a threaded portion 62 of an insulating portion 64 which surrounds connector 50 and which is also illustrated in FIG. 5.

As can be seen in FIG. 6 when the plug 58 is properly inserted into connector 52 an electrical path is established between the pins 56 through the connector. As will be discussed hereinafter with respect to the monitor circuitry, it is this electrical connection which is monitored to insure that dual lead 34 is properly connected to shield tube 20.

A latch 66, one example of which is shown in FIGS. 5 and 6, is preferably employed to secure the active probe in place after it has been inserted through the shield accessory 25, the latch being shown in its secured position in FIG. 6 and in its release position in FIG. 5. Other means may also be employed to releasably secure the active probe in place including a compression collett type lock. Note the tip of active probe may be positioned as desired by the user with respect to the distal end of shield accessory 25 before the latch is operated to latch the active probe in place with respect to the shield accessory. This adjustability feature is advantageous in that different accessories have different needs for the close spacing of the insulation with respect to the tip. Moreover, different surgeons may have different preferences with regard to their fields of view which is a variable. Furthermore, this feature may be utilized to adjustably limit the tip exposure.

Figure 8:
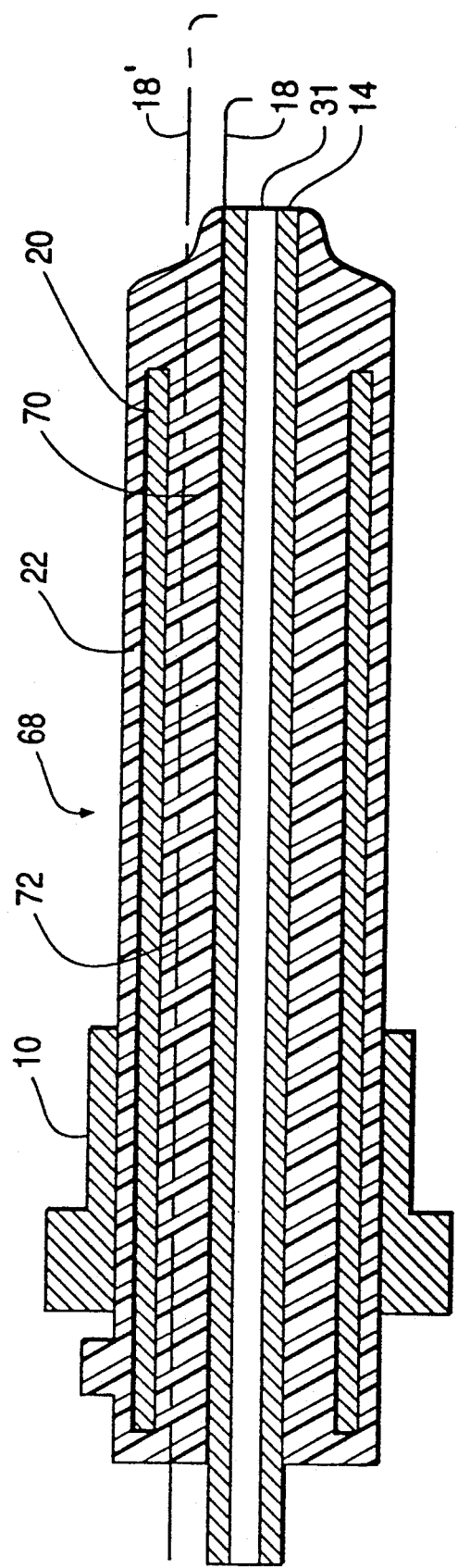
FIG. 8 is a cross-sectional view of a further embodiment of a laparoscopic electrosurgical apparatus in accordance with the present invention.

Referring to FIG. 8, there is shown a further embodiment of the invention where there is no (or minimal) insulation on active electrode 14. Extending through the active electrode is elongated port 31 through which irrigation fluids, suction, pressurized gas, etc. may pass. Moreover, port 31 may be utilized for various further functions such as gas-augmented-fulguration, a specialized field in which the safety shield of the present invention appears to be particularly advantageous. The safety shield assembly 68 includes shield 20 with insulation layer 22 on the outer surface thereof and insulation layer 70 on the inner surface thereof. Thus, insulation layer 70 provides the insulation between shield 20 and active electrode 14. Shield 68 is disposable (limited use) and as can be appreciated from the foregoing provides a complete insulation system which can be used with uninsulated trocar sheath 10 and uninsulated active electrode 14. Hence, since shield 22 is disposable (limited use), all insulation is replaced with each use or after a limited number of such uses. This embodiment also enhances cleanability since the reusable instrument does not have a permanent interface with the insulation. In this embodiment although no insulation is shown on active electrode 14 there may be a small amount if so desired.

In another embodiment of the invention as also illustrated in FIG. 8, the tubular electrode 14 may be eliminated and the active electrode extended through the insulating layer 70 as a conductor 72 as indicated by the phantom line where tip 18' is attached to the distal end of the conductor. This embodiment is advantageous in that the port 31 extending through sleeve assembly 68 may have its diameter widened to the outer diameter of removed electrode 14. Moreover, the number of separate parts is reduced to one with the elimination of removable electrode 14 and the incorporation of the conductor 72 within insulating portion 70.

Figure 9:
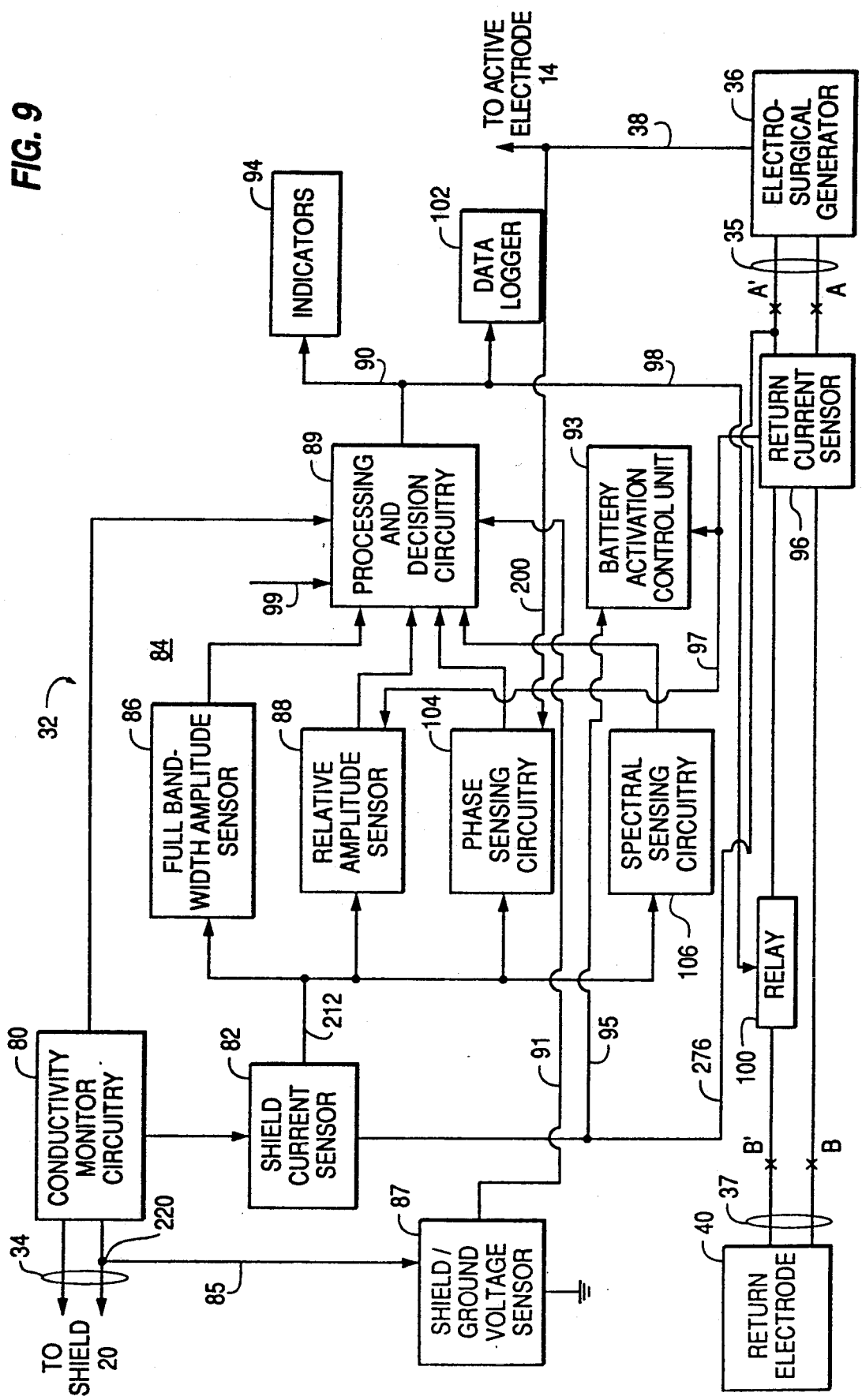
FIG. 9 is a generalized block diagram of illustrative monitor circuitry for use in the present invention.

Referring to FIG. 9, there is illustrated a generalized block diagram of the shield monitor circuitry 32 of FIG. 2. In particular, a conductivity monitor 80 is connected to dual lead 34, the purpose of the conductivity monitor circuit being to measure the integrity of the connection of lead 34 to shield 20. The dual connection provides a redundant path for shield monitoring current which is applied to lead 34 as will be described in more detail hereinafter with respect to FIG. 10.

A shield current sensor 82 senses the current passing from the shield 20 to return electrode lead 35, 37. The shield current sensor may provide a signal voltage proportional to the instantaneous value of the shield current as will be explained in more detail with respect to FIG. 10.

Measurement electronics circuitry 84 includes various circuits for measuring different parameters of at least the sensed shield current. The first of these circuits is a full bandwidth amplitude sensor 86 which measures the amplitude of the full bandwidth of the sensed shield current. A processing and decision circuit 89 determines whether this amplitude exceeds a predetermined threshold and if it does, a fault condition may be applied to indicators 94 over line 90. Indicators 94 may be aural and/or visible and provide an appropriate alert.

In addition to applying an alert signal over line 90, a generator deactivate signal is applied over line 98 to a relay 100 which opens the connection between return electrode 40 and generator 36 to thus deactivate the generator and discontinue the application of electrosurgical energy.

That is, the monitor circuitry 32, when used outside host electrosurgical generator 36 (as illustrated in FIG. 2), is preferably used with an electrosurgical generator of the type having a dual return electrode lead whereby the integrity of the return electrode connection can be monitored. Such monitoring circuitry is known whereby a split (or double) patient electrode is employed and a DC current (see German Patent No. 1139927 published Nov. 22, 1962) or an AC current (see U.S. Pat. Nos. 3,933,157 and 4,200,104) is passed between the split electrodes to sense patient contact resistance or impedance between the patient and the electrodes. If an open circuit condition is sensed, the generator is deactivated. Since the relay 100 of FIG. 9 is opened upon detection of a fault condition, the return electrode connection is also opened to thus deactivate the generator. However, it is to be understood other means will also occur to those skilled in this art for deactivating the generator upon detection of a fault condition by monitor circuitry 32.

A data logger 102 may also be connected to processing and decision circuitry 89 to provide a hard copy of various safety conditions.

Relative amplitude measurement circuitry 88 may be responsive to the ratio of the amplitudes of the sensed shield current and the sensed return electrode current as determined by return current sensor 96. Processing and decision circuitry 89 determines whether this ratio exceeds a predetermined threshold and if it does an alert signal is applied over line 90 while a deactivate signal is applied over line 98 to relay 100 in a manner similar to that described above with respect to the absolute amplitude fault condition.

Phase sensing circuitry 104 is responsive to the phase difference between the voltage applied to the active lead 38 of FIG. 2 and the sensed shield current. In FIG. 2 the monitor circuitry 32 is indicated as being housed outside host electrosurgical unit 36. However, it may also be incorporated within the electrosurgical generator. In the latter instance, access may be readily gained to the active voltage and thus the phase comparison made by phase sensing circuitry 104 can be readily effected. When the monitor is located outside of the host electrosurgical unit, it is somewhat more inconvenient to gain access to the applied voltage signal; nonetheless, appropriate means will occur to those of ordinary skill in the art to gain access to this signal.

Detection of the phase difference between the active voltage and the shield current is a particularly good indicator of a fault condition. That is, normal shield currents are exclusively capacitive—in particular, due to the capacitive coupling between active electrode 16 and shield 20, there is a 90° phase difference between the active voltage and the shield current under normal conditions. Hence, as long as the insulation between the active electrode and the shield is intact, a normal condition will be sensed by phase sensing circuitry 104 where the phase circuitry may be of the type shown in FIG. 11 as will be described in more detail hereinafter.

In general, the phase sensing circuitry, in response to the phase difference between the applied inputs being 90°, provides a first output (high voltage, for example). If there is an insulation breakdown between the active electrode 16 and the safety shield 20, arcing will typically occur and such arcing currents are almost exclusively in phase with the applied voltage. That is, the shield current will be in phase with the active voltage. Phase sensing circuitry 104 detects this in phase, fault condition to change the output from high to low.

Spectral sensing or filtered bandwidth circuitry 106 provides a further reliable means for detecting the presence of arcing between the active electrode and shield. Moreover, this method does not need access to the active electrode voltage and thus readily lends itself to those monitor circuits 32 which are located outside the host electrosurgical generator 36. As will be described in more detail hereinafter with respect to FIG. 10, spectral sensing circuitry is responsive to at least one predetermined bandwidth of the sensed shield current to detect the presence of a shield current produced by arcing where the arcing will typically occur between the active electrode and the shield due to insulation breakdown therebetween.

Both the phase sensing circuitry 104 and the spectral sensing circuitry 106 also apply inputs to processing and decision circuitry 89 in a manner similar to that described above with respect to circuits 86 and 88 whereby the outputs of circuits 104 and 106 may be utilized to actuate indicators 94 and data logger 102 and deactivate the electrosurgical generator via relay 100.

As indicated above, one or more of the sensing circuits 86, 88, 104, and 106 may be independently utilized or utilized in combination to effect the shield monitor function of circuitry 32.

Various measures have been taken in the present invention to render the operation thereof fail-safe. For example, if the monitor circuitry 32 is employed outside host electrical generator 36, there is a possibility the user may connect the return electrode directly into the electrosurgical generator rather than through the monitor circuitry 32 as illustrated in FIG. 2. If this occurs, the shield will not be connected to the return electrode lead through a low impedance path, as will be discussed below, and thus monitor circuitry 32 will be inhibited from performing its monitoring function. To provide an alert to the user that the return electrode has been inappropriately directly connected to the generator 36, a shield to ground voltage sensor 87 may be provided, the sensor 87 being responsive to the shield voltage over line 85 via cable 34. The output of shield/ground voltage sensor 87 is applied to processing and decision circuitry 89 where an appropriate indicator 94 is actuated if the return electrode is directly connected to the electrosurgical generator.

If the return electrode is directly connected to the electrosurgical generator, the voltage on the shield will rise to a substantial percentage of the active voltage in view of an open circuit between the shield and the return electrode lead. Hence, whenever the voltage on the shield exceeds a predetermined threshold as will be discussed in more detail with respect to FIG. 12, an appropriate signal is applied to processing and decision circuitry 88 over line 91 to thereby provide a desired alert.

Furthermore, when the monitor circuitry 32 is provided outside host electrical generator 36, it is desirable in some instances to battery power the monitor circuitry 32. That is, if the monitor circuitry is powered from an operating room electrical outlet, this will entail an additional wire being connected to the monitor circuitry where in some instances it is desirable that the number of wires associated with the electrosurgical apparatus be reduced to a minimum. Accordingly, an activation control unit 93 may be employed which is responsive to the sensed shield current over line 95 or the sensed return current over line 97 to provide a battery power supply for the various circuits of monitor circuitry 32 as will be described in more detail hereinafter with respect to FIG. 13.

Figure 10:
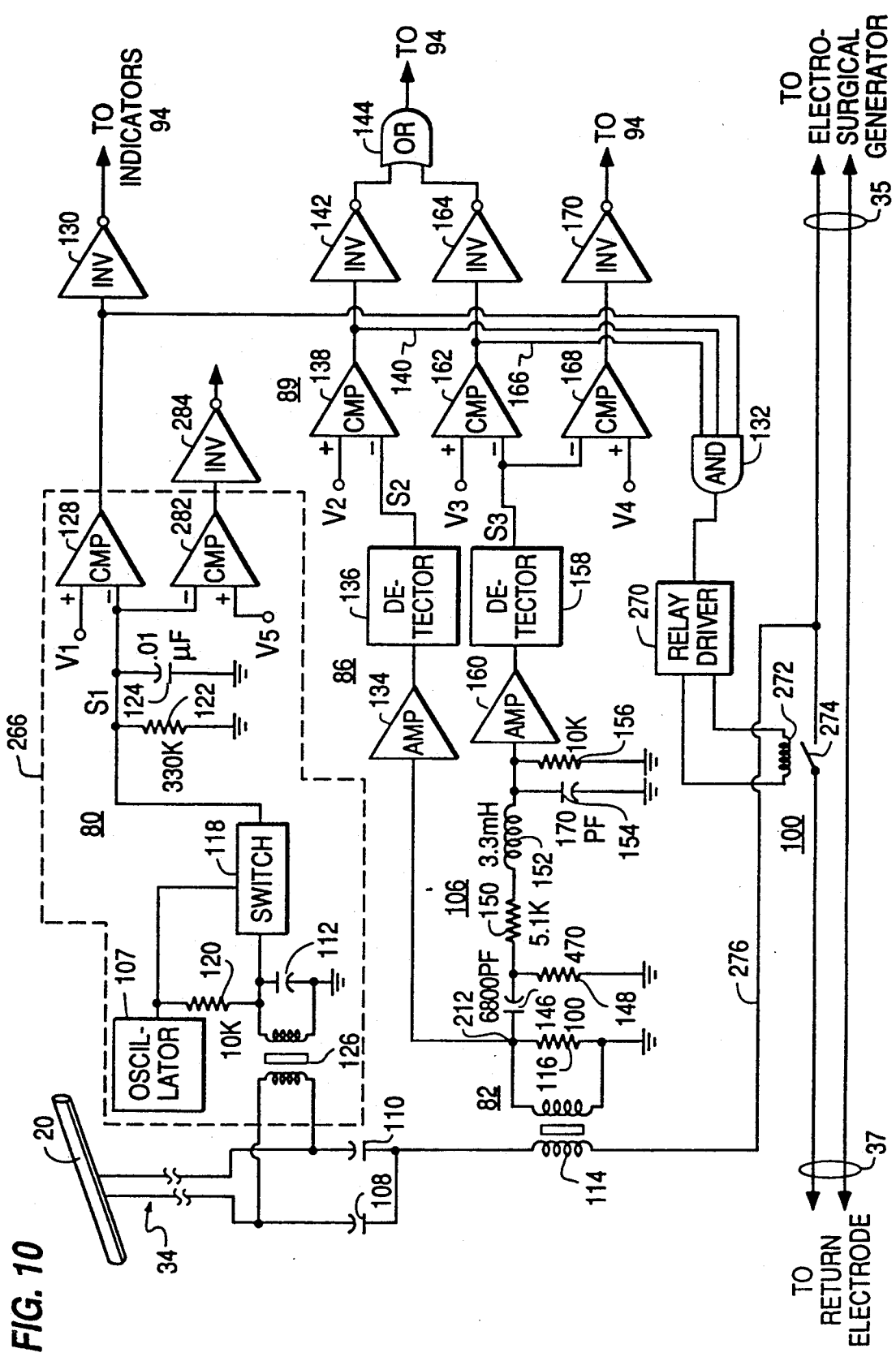
FIG. 10 is a schematic diagram of the monitor circuitry of FIG. 9 where full bandwidth amplitude and spectral sensing (or filtered bandwidth) measurement circuitry are illustrated in further detail.

In FIG. 10, the full bandwidth amplitude sensor 86 and the spectral sensing circuitry 106 of FIG. 9 are illustrated in further detail together with the conductivity monitor 80 for monitoring the integrity of the connection of shield connector 34. The conductivity monitor 80 comprises a square wave oscillator 107 which is tuned to resonance with a network of capacitors 108, 110 and 112. The path from shield 20 to the return electrode lead comprises cable 34, capacitors 108 and 110, transformer 114, and resistor 116. This path has a low impedance—typically less than 20 ohms, to thus provide a low impedance pathway for any current coupled to shield 20.

A switch 118 is driven in phase with the voltage across capacitor 112 as it responds to oscillator 106. A resistor 120 connects the oscillator to capacitor 112. Resistor 122 and capacitor 124 provide a voltage $S_1$, the amplitude of which is inversely proportional to the amplitude of the monitor current provided by oscillator 107 through the redundant cable 34.

In operation, the oscillator applies a signal of approximately 15 KHz to capacitor 112 via resistor 120. This signal is coupled by transformer 126 across dual redundant cable 34. As long as the cable 34 is properly connected to shield 20 a path will be provided for the oscillator signal which will be reflected back through transformer 126. Since switch 118 is operated at the frequency of oscillator 107, the signal reflected back through transformer 126 will be synchronously detected at 118 and applied to the demodulator comprising resistor 122 and capacitor 124 where switch 118 may a 4066 transmission gate or an FET. The electrosurgical frequency (typically 750 KHz although other electrosurgical frequencies may be employed) will be rejected by the synchronous detector and thus conductivity monitor 80 is sensitive only to the conductivity monitoring signal generated by oscillator 107.

As long as the cable 34 is properly connected to shield 20, the signal amplitude developed at capacitor 124 will be less than the reference voltage $V_1$ established applied to comparator 128. Accordingly, the output of comparator 128 will be high during this time and the output of inverter 130 will be low and thus no alert will be provided by indicators 94 of FIG. 9. The function of comparator 282 and inverter 284 will be described hereinafter.

If the cable 34 is not properly connected to shield 20, the voltage developed across capacitor 124 will exceed the reference voltage $V_1$ and thus the output of comparator 128 will go low and the output of inverter 130 will go high to thereby generate a fault alert "connection" at indicators 94 of FIG. 9.

The output of comparator 128 is also applied to an AND circuit 132 which in turn is connected to relay 100. As long as all the inputs to AND circuit 132 are high, a signal will be applied to relay coil 272 via relay driver 270 to thus close the contact 274 of relay 100 and establish the connection between the return electrode and the return terminal of the generator. If the output of comparator 128 goes low because of a faulty connection of cable 34 to shield 20, the output of AND circuit 132 will go low to thus de-energize relay 100 and thus prevent activation of the generator until the cable is properly connected to the shield.

The shield current sensor 82 of FIG. 9 comprises transformer 114 and resistor 116. The full bandwidth amplitude sensor 86 comprises an amplifier 134 and a detector 136. Thus, the unfiltered shield current sensed at 82 is converted to a proportional voltage by detector 136 where the output of detector 136 is applied to a comparator 138. As long as $S_2$, the output of detector 136 does not exceed reference voltage $V_2$, the output of comparator 138 remains high to thus enable AND circuit 132 over line 140. If the value of the sensed shield current exceeds the threshold established by $V_2$, the output of comparator 138 will go low to thus disable AND circuit 132 and thus de-energize relay 100 thereby deactivating the electrosurgical generator. Moreover, if the output of comparator 138 goes low the output of inverter 142 will go high as will the output of OR circuit 144 to thus generate a fault alert "shield current" at indicators 94 of FIG. 9.

Spectral sensing or filtered bandwidth circuitry 106 comprises a band pass filter, the band pass at the 3 db points of which are about 50 KHz to 250 KHz. The filter comprises a capacitor 146, a resistor 148, a resistor 150, an inductor 152, a capacitor 154, and a resistor 156.

The filter may be of the Butterworth or any other suitable type to effect the desired band pass function.

The output of the filter is applied to a detector 158 through a amplifier 160 where detector 158 generates a signal proportional to the signal energy passed by the filter. Detectors 136 and 158 may be RMS to DC convertors such as the LT 1088 made by Linear Technology, Inc.

As indicated above, a typical electrosurgical operating frequency is about 750 KHz while other operating frequencies such as 500 to 750 KHz may also be employed in accordance with the invention although there is no intent to be limited to a particular operating frequency. The bandpass of 50 to 250 KHz is particularly indicative of whether an arcing current is present although other bandpasses may be used as long as they are appropriately indicative of whether an arcing current is present.

If the output of detector 158 exceeds a first threshold voltage $V_3$ applied to a comparator 162, the output of the comparator will be switched from its normal high condition to a low condition such that a high signal will be provided at the output of OR circuit 144 through inverter 164 to thereby provide a fault alert "shield current" to indicators 44 of FIG. 2. Moreover, AND circuit 132 will be disabled over line 166 to thus de-energize relay 100 and deactivate the electrosurgical generator.

The output of detector 158 is also applied to a comparator 168, the threshold voltage $V_4$ of which is less than $V_3$. Thus, if the output $S_3$ of detector 158 exceeds $V_4$ but does not exceed $V_3$, this is an indication that the insulation between active electrode 14 and shield 20 is beginning to break down but has not completely broken down (where complete breakdown corresponds to reference $V_3$). Accordingly, in this situation where $S_3$ exceeds $V_4$ but not $V_3$, the output of comparator 168 will be switched from its normal high condition to a low output. The low output is inverted at inverter 170 to thus provide a warning alert at indicators 94 of FIG. 9.

The full bandwidth amplitude sensor 86 need not necessarily be employed inasmuch as the bandpass filter of spectral sensing circuitry 106 does have some response at the operating frequency where the operating frequency for the filter of FIG. 10 would typically be about 500 to 750 KHz. Therefore, the filter is sensitive to the high currents flowing during an insulation breakdown. Accordingly, the spectral sensing circuitry 106 of FIG. 10 can also perform the full bandwidth amplitude sensing function of circuitry 86. In this regard, it should be noted, insulation breakdowns tend to produce high shield currents. Moreover, normal shield current is also rather large where the normal shield current is capacitively coupled to the shield from the active electrode, as discussed above with respect to phase sensing circuitry 104. Hence, the normal and fault currents can be rather close to one another in absolute amplitude. The range of currents in one embodiment under normal conditions has been measured to be about 50 to 250 ma RMS depending upon the quality of insulation used, the type of waveform applied, and the control setting of the generator. Fault condition currents in this embodiment may be in the range of 300 to 1500 ma RMS. The closeness of these limits leads to difficulty in some situations in distinguishing between normal and fault conditions if the determination is based on absolute RMS current alone as detected by sensor 86. However, testing has demonstrated that with a band pass filter such as the filter of spectral sensing circuitry 106, the differentiation is substantially improved. For a "coagulation" waveform, where breakdown is most likely, there is typically a 4:1 differentiation between the top of the normal range and the bottom of the abnormal range. Accordingly, the spectral sensing circuitry 106 is very reliable in detecting an arcing current indicative of insulation breakdown.

With respect to the processing and decision circuitry 89 of FIG. 9, it should be noted that the comparators 128, 138, 162 and 168, the inverters 130, 142, 164 and 170, AND circuit 132, and OR circuit 144 comprise the elements of FIG. 10 which correspond to circuitry 89, there being no intent to limit the invention to this particular decision circuitry.

Illustrative values are given for certain components of FIG. 10 and other figures of the drawing where resistance is in ohms. There is no intent to limit the invention to these values.

Figure 11:
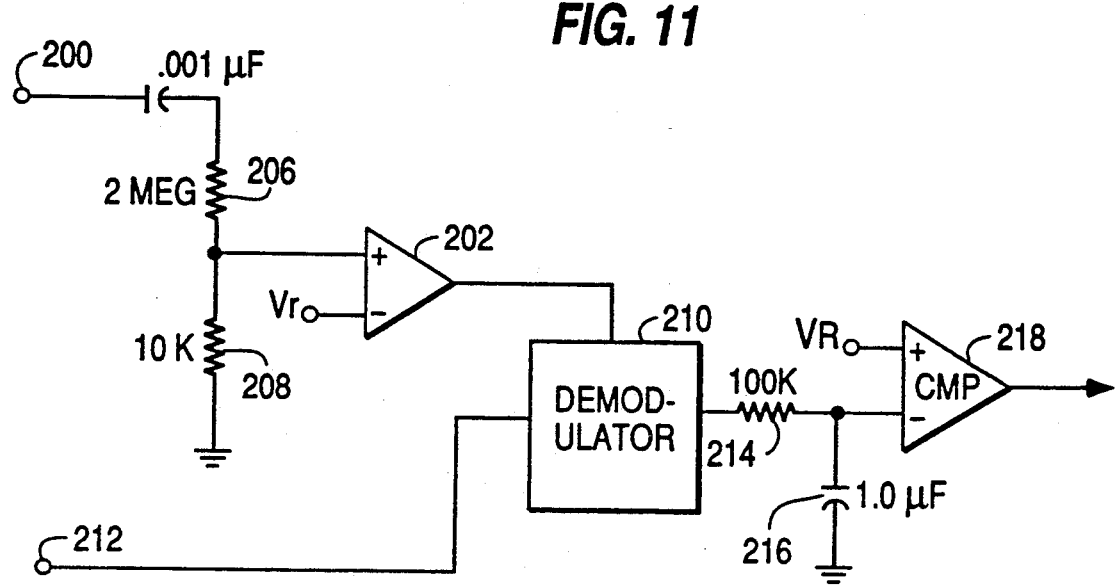
FIG. 11 is a schematic diagram of illustrative phase sensing circuitry for use in the invention.

Referring to FIG. 11, there is illustrated in further detail the phase sensing circuitry 104 of FIG. 9. The active electrode voltage is applied to terminal 200 and coupled to the positive terminal of a comparator 202 via a capacitor 204 and a voltage divider comprising resistors 206 and 208. The reference voltage $V_r$ applied to the negative terminal of comparator 202 is such as to provide a substantially square wave signal at the output of comparator 202, the frequency and phase of which corresponds to that of the active voltage applied to terminal 200 where this square wave signal is applied to an input of a demodulator 210 which may be an analog transmission gate such as a Motorola MC 1596.

Applied to the second input of the demodulator is the sensed shield current which corresponds to the voltage across resistor 116 of FIG. 10 at terminal 212. The output of the demodulator is applied to an RC circuit comprising resistor 214 and capacitor 216 where the output of the RC network is applied to the negative input of a comparator 218. Applied to the positive input of the comparator is reference voltage $V_R$, which may be adjusted to correspond to approximately 100 ma of shield current in phase with the active voltage. Thus, in an arcing situation (corresponding to damaged installation or the like), the shield current will be in phase with the active voltage, as discussed above, whereby the voltage across capacitor 216 will exceed the reference voltage $V_R$ to thus switch the output of converter 218 from high to low.

Assuming the phase sensing circuitry 104 is employed rather than the spectral sensing circuitry 106, the switching of the output of comparator 218 from high to low would deactuate AND circuit 132 to open relay 100 whereby the generator would be deactivated and an alert condition would be applied from the output of OR circuit 144 to appropriate indicators 94.

Figure 12:
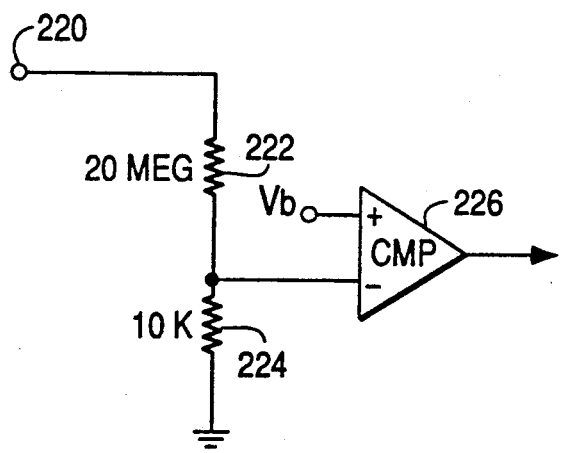
FIG. 12 is a schematic diagram of illustrative shield-to-ground voltage sensing circuitry in accordance with the invention.

Referring to FIG. 12, the shield/ground voltage sensor 87 is illustrated in further detail where the voltage at terminal 220 is the voltage on shield 20, as indicated in FIG. 9. This voltage is applied through a voltage divider comprising resistors 222 and 224 to the negative input of a comparator 226. The resistor 222 is preferably rated to withstand the high voltage which may occur on the shield if the monitor circuitry 32 is not connected to the return electrode whereby, as discussed above with respect to FIG. 9, the voltage on the shield will approach the full active voltage. Connected to the positive input of comparator 226 is a reference voltage $V_b$ where $V_b$ in a typical application corresponds to 100 to 300 volts on shield 20. That is, the voltage $V_b$ may be approximately 0.5 to 1.5 volts.

In operation, whenever the voltage applied to the negative input of comparator 226 exceeds the reference voltage $V_b$, the output of the comparator will change from its normal high level to a low level whereby a fault alert may be generated at the output of OR circuit 144 as described above and a generator deactivate signal may be generated at the output of AND circuit 132 as also described above with respect to the phase sensing circuitry.

Figure 13:
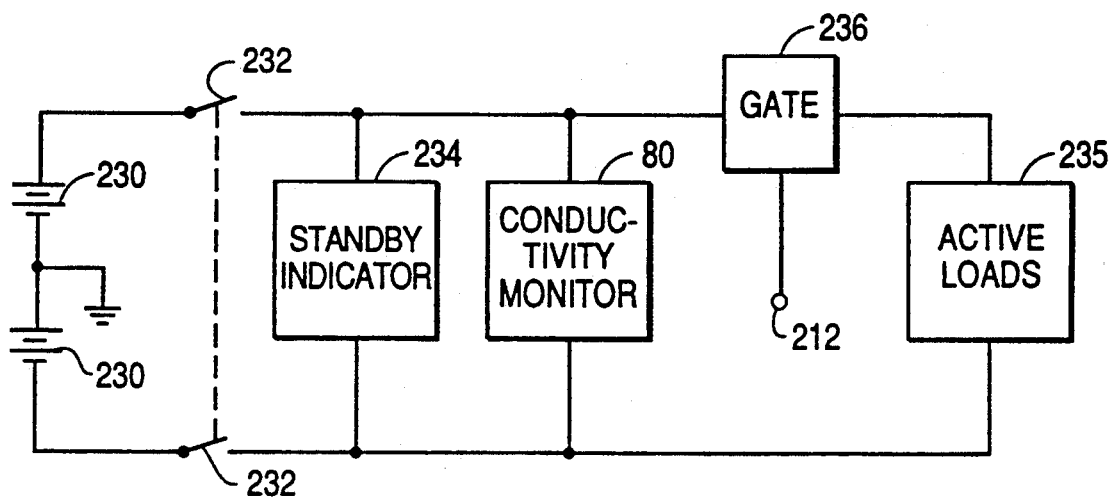
FIG. 13 is a schematic diagram of illustrative battery activation control circuitry in accordance with the invention.

Referring to FIG. 13, there is illustrated battery activation control unit 93 of FIG. 9 which includes batteries 230, ganged switches 232, standby indicator 234, and gate 236. In operation, switches 232 are closed in response to shield cord 34 being connected to shield monitor circuitry 32. Although means are not specifically shown, such means are known whereby upon insertion of a plug into a circuit, a switch may be mechanically closed to effect a further function and such means would be employed to close ganged switches 232 in response to the shield cord being connected to monitor circuitry 32.

Upon closure of switches 232, standby indicator 234 is actuated to indicate a standby status of the monitor circuitry 32. Moreover, the voltage from batteries 230 is applied to conductivity monitor circuitry 80 of FIG. 9 whereby the conductivity monitor may provide an indication to the user that cable 34 has been properly connected to shield 20. If not, an alert is provided to the user as described above with respect to conductivity monitor 80.

Moreover, the voltage from batteries 230 is applied to gate 236 as a power supply voltage therefore whereby the gate 236 is primed to apply the voltages from batteries 230 as power supply voltages to the remaining circuits of the monitor 32 of FIG. 9 which are illustrated as active loads 235 in FIG. 13. That is, gate 236 is responsive to the sensed shield current established at terminal 212 of FIG. 10. As soon as this current is sensed, all of the circuits of the monitor are powered by batteries 230.

Another consideration relating to fail-safe operation is that, when the shield monitor circuitry 32 is utilized outside the host electrosurgical generator, the shield must not become the return electrode. Accordingly, an adaptor, as schematically illustrated in FIG. 14, may be utilized to insure that the return electrode is properly connected to the monitor circuitry 32.

Figure 14:
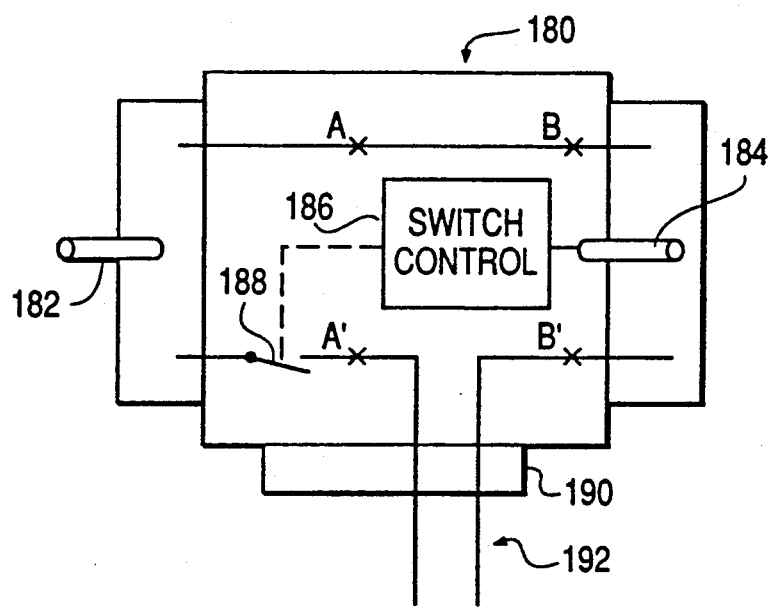
FIG. 14 is a schematic diagram of an illustrative adaptor for use with the shield monitor circuitry of this invention.

In particular, referring to FIG. 14, the adaptor is indicated at 180 and includes a pin 182 which connects to the return terminal of the electrosurgical generator in a conventional manner to indicate to the generator the use of a dual-area return electrode. That is, pin 182 corresponds to a pin employed in an industry standard connector whereby the generator will not operate until the return electrode is properly connected to the return terminal of the generator.

Receptacle 184 of adaptor 180 is adapted to receive the above-mentioned standard pin of the return electrode plug. In a manner similar to that conventionally employed in the generator, the adaptor 180 includes a switch control mechanism 186 which is responsive to the insertion of the return electrode plug pin into receptacle 184 to close a switch 188 in the adaptor and thus close the connection of the return electrode to the electrosurgical generator through the adaptor.

The adaptor 180 additionally includes a port 190 by which the adaptor can be connected to monitor circuitry 32 via a two wire cord 192. When the cord is connected to the monitor circuitry 32, the points A, A' and B, B' shown in FIG. 14 respectively correspond to the same points shown in FIG. 9 where return current sensor 96 and relay 100 are incorporated in monitor circuitry 32 and switch 188 is incorporated in adaptor 180 and where cord 192 is not shown in FIG. 9.

Thus, unless the return electrode 40 is connected to adaptor 180 via receptacle 184, switch 188 will not be closed and hence the generator can not be activated even though pin 182 of the adaptor is properly connected to the generator. Accordingly, the shield cannot become the return electrode. Moreover, if use is attempted without the return electrode plug pin being inserted into receptacle 184, a fault condition may be presented at indicators 94. That is, a signal may be generated by means (not shown) over line 99 of FIG. 9 and applied to circuitry 89 where the signal is generated depending on the position of switch 188.

Figure 15:
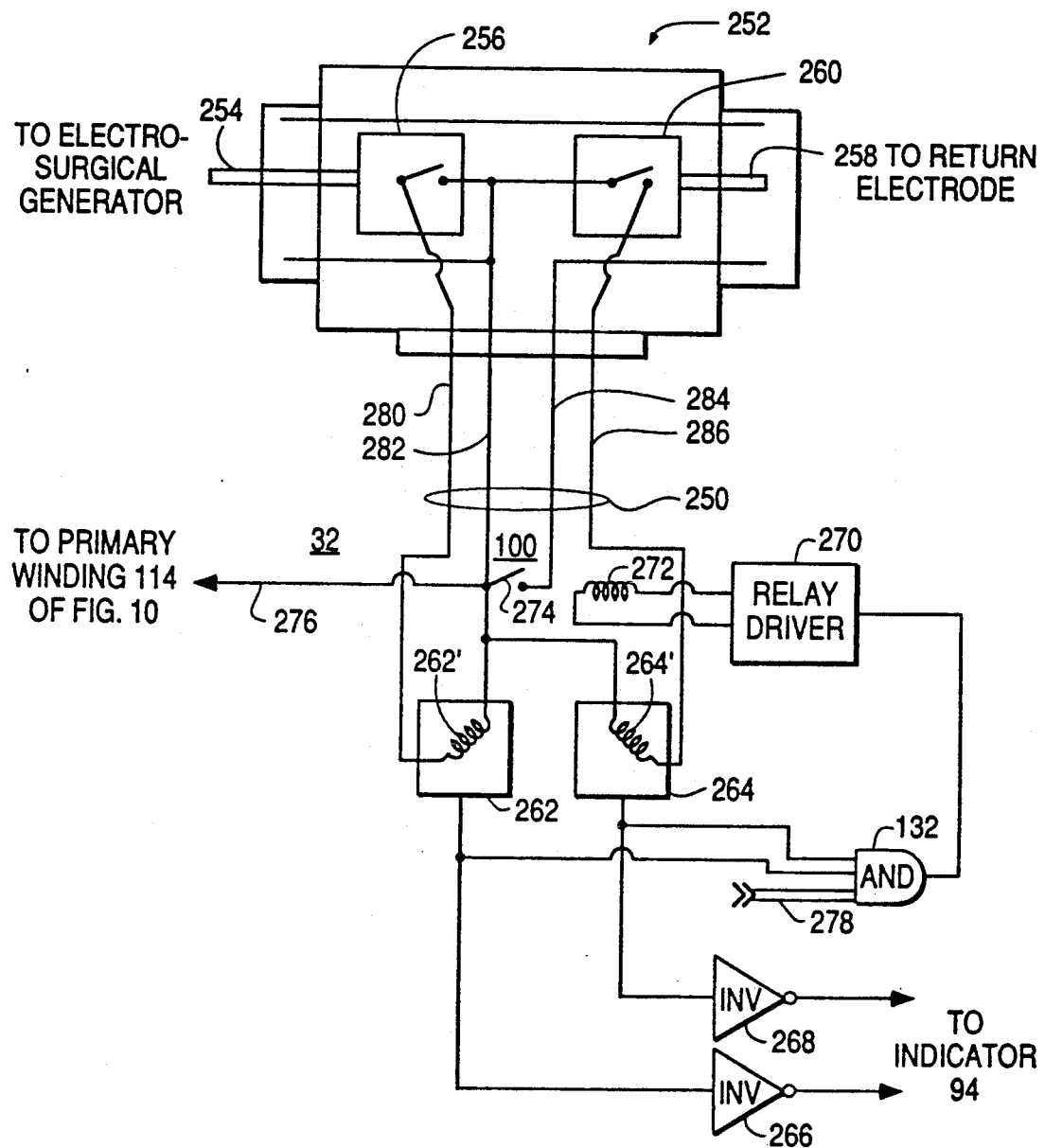
FIG. 15 is a schematic diagram of another illustrative adaptor together with further illustrative shield monitor circuitry for use in this invention.

In the embodiment of FIG. 15, a four wire connection or cord 250 is utilized between an adaptor 252 and monitor circuitry 32 where the monitor circuitry is partially indicated at 32 in FIG. 15 as will be described in more detail below. Adaptor 252 includes a pin 254 which corresponds to pin 182 of adaptor 180 of FIG. 14. Moreover, pin 254 is associated with a switch 256 whereby the switch 256 is closed in response to adaptor 252 being attached to the return terminal of the electrosurgical generator. Adaptor 252 also includes a receptacle 258 which corresponds to receptacle 184 of adaptor 180. Thus, adaptor 252 includes a switch control mechanism (not shown), which is responsive to the insertion of the return electrode plug pin to close a switch 260 in the adaptor.

The adaptor 252 further differs from adaptor 180 in that in adaptor 180, switch 188 is in series with one of the generator return leads whereas in adaptor 252 the switches 256 and 258 are referenced to this lead.

In order to detect proper connection of adaptor 252 to the generator via switch 256 and proper connection of the return electrode to the adaptor via switch 260, continuity monitors 262 and 264 are provided where each of these monitors corresponds to the continuity monitor circuitry indicated at 266 in FIG. 10 within the dotted lines. The output of each continuity monitor is applied to AND gate 132, which is shown in both FIGS. 10 and 15. The output of AND circuit 132 is applied to relay driver 270 which drives the coil 272 to, in turn, actuate the contact 274 of relay 100. The outputs of the continuity monitors are also applied to inverters 266 and 268 respectively. The outputs of inverters 266 and 268 are applied to appropriate indicators 94.

When the adaptor 252 of FIG. 15 is employed, the shield return lead 276 is connected to the generator return lead as shown in FIGS. 9, 10, and 15. Thus, when the adaptor 252 is employed, four separate transformers are incorporated in monitor circuitry 32 where two of these transformers correspond to transformers 114 and 126 of FIG. 10 and the other two transformers are associated with conductivity monitors 262 and 264, the primaries of these transformers being indicated at 262' and 264'. In particular, the primary windings 262' and 264' each serve the same function as the primary of transformer 126; thus, when the monitor circuitry 32 is employed with adaptor 252 of FIG. 15, the monitor circuitry will incorporate three separate conductivity monitors—that is, conductivity monitor 80 (shown in FIG. 10) and the conductivity monitors 262 and 264 of FIG. 15.

In operation, the adaptor 252 provides fail-safe operation in that if the adaptor is not properly connected to the generator, AND circuit 132 will be disabled to thus present this fault condition at indicators 94. In particular, if switch 256 is open, thereby indicating lack of attachment of the adaptor to the return terminal of the generator, an open circuit condition will exist across the primary 262' to thus provide a low output signal from conductivity monitor 262, as described hereinbefore with respect to conductivity monitor 80 of FIG. 10. This in turn will present this fault condition at indicators 94.

In a similar manner, if the return electrode is not connected to the adaptor, switch 260 will be open to thus provide an open circuit condition across the primary winding 264'. Accordingly, the output of conductivity monitor 264 will go low to disable AND circuit 132 and open relay 100 and to present this fault condition at indicators 94. The additional inputs to AND circuit 132 shown in FIG. 10 are indicated at 278 in FIG. 15.

It should be noted that the particular situation that switch 256 protects against is that where a first return electrode lead is inadvertently directly connected to the generator and a second return electrode lead is connected to receptacle 258 of adaptor 252. However, contact 274 of relay 100 of adaptor 252 is not connected to the return electrode circuit of the generator and thus monitor 32 can not disable the generator. However, switch 256 will warn against the foregoing situation by providing an appropriate alert at indicator 94.

If it is considered not necessary to protect against this situation, switch 256 need not be incorporated in adaptor 252. In this case, switch 256 and wire 280 would be eliminated together with conductivity monitor 262. Thus, the resulting connection between adaptor 252 and monitor circuitry 32 would be a three wire cord comprising wires 282, 284 and 286 where switch 260 is referenced to one of the generator return leads.

As described above, and as will be further described hereinafter, various circuits may be employed to provide fail-safe operation of shield monitor circuitry 32. Thus, as stated above, the circuitry of FIG. 15 utilizes four transformers to monitor various conditions. Moreover, the number of transformers may be reduced while still monitoring the same number of conditions by having each condition correspond to a particular frequency and thus detecting each condition by appropriate frequency discrimination circuitry. Other techniques will also occur to those of ordinary skill in this art.

As discussed above, one of the conditions which may be protected against to provide fail-safe operation includes the shield 20 not being connected to the shield monitor where shield continuity monitor 80 of FIG. 10 provides this fail-safe function. Moreover, by employing an additional comparator 282 (FIG. 10), it is possible to monitor not only a lack of connection of the shield to monitor circuitry 32 but also a poor connection. Reference voltage $V_5$ is applied to comparator 282 and is less in magnitude than the reference $V_1$ applied to comparator 128. Thus, comparator 282 detects a poor connection if the voltage across capacitor 124 exceeds $V_5$ but is less than $V_1$ whereby the output of comparator 282 goes low and is inverted by inverter 284 to provide an indication of the poor connection.

When the adaptor 252 of FIG. 15 is not plugged into the return terminal of the generator but rather the return electrode is improperly directly attached to the return terminal, this will be detected inasmuch as switch 260 of FIG. 15 will not be closed whereby indicators 94 will provide an appropriate alert.

Figure 16:
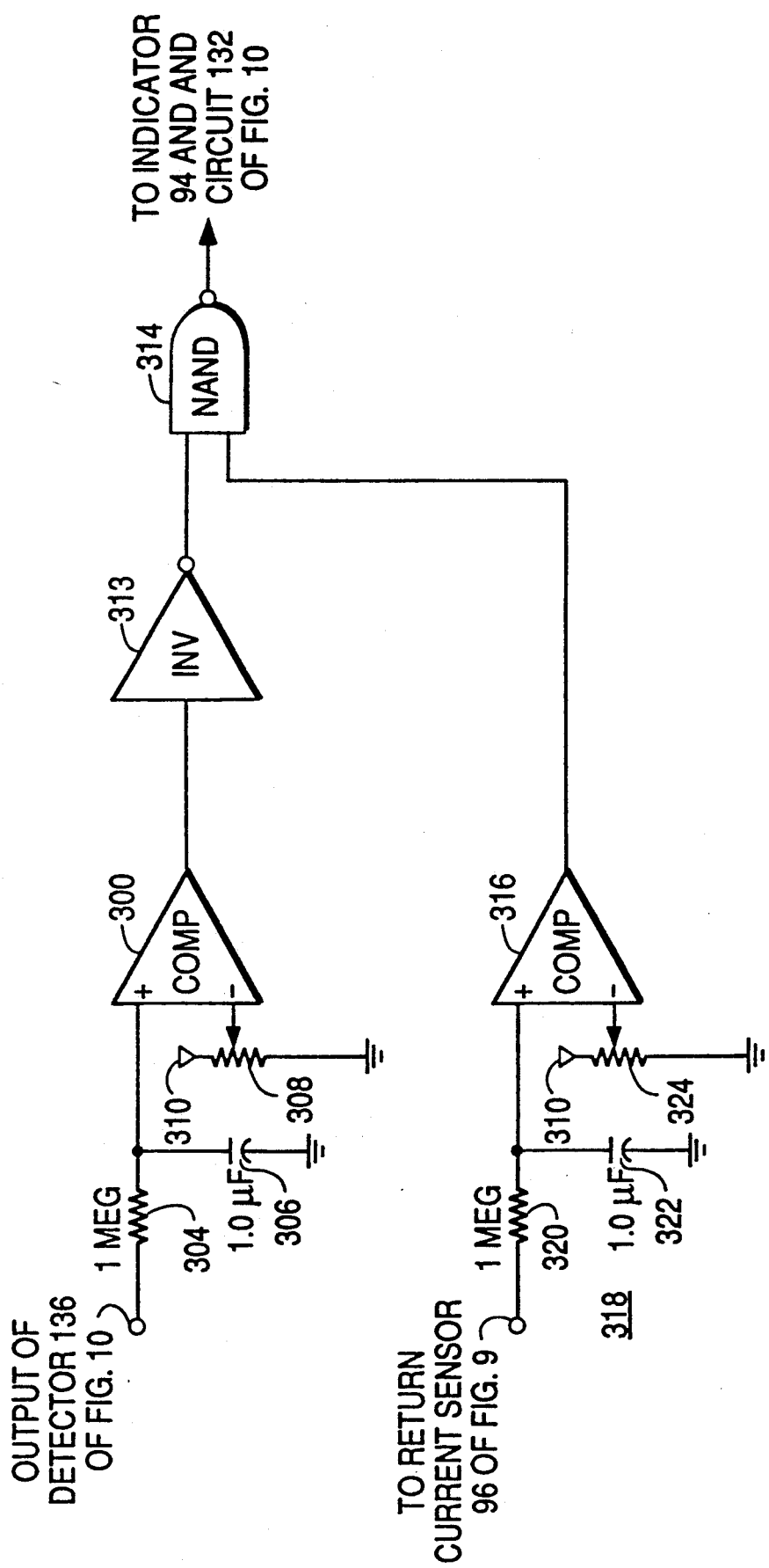
FIG. 16 is a schematic diagram of illustrative circuitry for protecting against failure to insert an accessory into a shield properly connected to the monitor circuitry.

Referring to FIG. 16, there is illustrated further protection circuitry in accordance with the invention to protect against the possibility of a user properly connecting the shield to monitor circuitry 32 and the monitor circuitry to generator 36 but not inserting the accessory (or active electrode 14) properly into the connected shield. The accessory would instead be inserted directly into trocar sheath or cannula 10 without a shield or it might be used with a different shield, not the one connected to the monitor. In accordance with the embodiment of FIG. 16, the foregoing possibility is protected against by requiring at least a predetermined minimum amount of shield current to be present when the generator is activated.

If the monitor is disposed within the electrosurgical unit whereby the voltage on the active lead (that is, the voltage between the active and return leads) is readily accessible, the foregoing protective function can be accomplished by sensing a predetermined minimum amount of shield current in the presence of the active lead voltage. The presence of active lead voltage without the predetermined minimum amount of shield current would be interpreted as a fault condition. If monitor unit 32 is disposed outside the electrosurgical generator, the active voltage is less readily accessible and thus the return current may be utilized if the active lead voltage is not sensed. This latter technique is illustrated in the circuitry of FIG. 16.

In FIG. 16, the sensed shield current is obtained from terminal 212 of FIG. 10 and applied to the positive input of a comparator 300 via a filter 302 comprising resistor 304 and capacitor 306. Applied to the negative input of comparator 300 is a reference voltage obtained from potentiometer 308 connected between reference voltage source 310 and ground. The comparator output is applied via invertor 313 to an input of a NAND circuit 314.

The sensed return current is obtained from return current sensor 96 of FIG. 9 and applied to the positive input of a comparator 316 via a filter 318 comprising resistor 320 and capacitor 322. Applied to the negative input of comparator 316 is a reference voltage via a potentiometer 324 connected between reference voltage source 310 and ground. The output of comparator 316 is applied to a second input of NAND circuit 314. The output of NAND circuit 314 is applied to indicators 94 and AND circuit 132 of FIG. 10 to thus provide an appropriate alert of the foregoing condition together with deactivation of the generator.

The filters 302 and 318 are provided because high value of the shield current may not occur at precisely the same time as high value of the return current. For example, a loaded generator may produce high return current but not high shield current. Thus, by storing the sensed values of the shield and return currents with respective filters 302 and 318, it is possible to utilize the return current rather than the active voltage to sense the foregoing condition where the accessory is not properly inserted into a connected shield. In general, the time constants of filters 302 and 318 should be as long as the typical activation period of an electrosurgical generator—that is, about 2 to 3 seconds. Other than filters 302 and 318, more sophisticated methods of signal processing may also be utilized such as peak detection within a time window.

In operation, a high output from NAND circuit 314 indicates a normal condition where the shield current is present in the presence of the return current. Thus, if sensed return current is applied to the positive input of comparator 316 to exceed the threshold established by potentiometer 324, the output of comparator 316 goes high and is applied to NAND circuit 314. Moreover, if sensed shield current is applied to the positive terminal of comparator 300, such that the threshold established by potentiometer 308 is exceeded, the output of the comparator goes high and the output of inverter 313 goes low whereby the output of NAND circuit stays high. However, if there is no shield current which exceeds the threshold established by potentiometer 308, the output of comparator 300 will remain low while that of inverter 313 will remain high. Hence, in this situation both of the inputs to NAND circuit 314 will be high causing the output of the NAND circuit to go low and thus indicate the above described fault condition.

As described above, the present invention is particularly advantageous in that it provides a shield between the trocar sheath and the active electrode whereby the shield may be utilized to effect essentially fail safe operation in electrosurgical laparoscopic procedures. Moreover, the deployment of the safety shield of the present invention may be extended to other procedures where a trocar is not used. For example, in tonsillectomies, the instrument is hand-held and inserted through the mouth, there being no need for a trocar. In addition to tonsillectomies, other similar procedures are deep pelvic procedures requiring long extensions and arthopedic and thoracic procedures, etc. With such hand-held instruments, the element 10, which corresponds to a trocar sheath in FIG. 2 and the other figures of the drawing, may instead correspond to the handpiece of a hand-held instrument—that is, that portion of a hand-held instrument which is held by the surgeon's hand. All of the advantages described above with respect to laparoscopic and like procedures are also realized with hand-held instruments used in open procedures such as laparotomy where again, the shield is connected through a low impedance path to the return electrode and where shield current monitor circuitry 32 is preferably utilized to achieve effectively fail-safe operation.

What is claimed is:

1. An electrosurgical apparatus comprising:
a handpiece having a tubular passage extending therethrough, the handpiece having a proximal end and a distal end;
a tubular conductive shield having an inner surface and an outer surface and being removably insertable through the handpiece passage to an inserted position, said shield having a layer of electrical insulation disposed at least over the outer surface thereof;
an active electrode probe having a tip and being adapted for connection to an electrosurgical generator and extending through the tubular conductive shield for effecting at the tip thereof an electrosurgical procedure where, when the tubular shield is in the inserted position thereof, the shield surrounds the active probe from at least (a) a proximal point prior to the proximal end of the handpiece to (b) a distal point distal to the distal end of the handpiece and in proximity to the tip of the active probe;
at least one layer of electrical insulation disposed between the active probe and the tubular shield; and
an electrical terminal connected to the shield and adapted for connecting the shield to a reference potential;
whereby any current which flows in said shield from said active probe is conducted to said reference potential to thus lessen a risk of patient injury due to an abnormal condition.

2. An electrosurgical apparatus comprising:
a trocar cannula having a tubular passage for providing a conduit through a patient's skin where the trocar cannula has a proximal end and a distal end;
a tubular conductive shield having an inner surface and an outer surface and being removably insertable to an inserted position through the trocar cannula conduit, said shield having a layer of electrical insulation disposed at least over the outer surface thereof;
an active electrode probe having a tip and being adapted for connection to an electrosurgical generator and extending through the tubular conductive shield for effecting at the tip thereof an electrosurgical procedure within a patient's body where, when the tubular shield is in the inserted position thereof, the shield surrounds and is electrically insulated from the active probe from at least (a) a proximal point prior to the proximal end of the trocar cannula to (b) a distal point distal to the distal end of the trocar cannula and in proximity to the tip of the active probe;
at least one layer of electrical insulation disposed between the active probe and the tubular shield; and
an electrical terminal connected to the shield and adapted for connecting the shield to a reference potential;
whereby any current which flows in said shield from said active probe is conducted to said reference potential to thus lessen a risk of patient injury due to an abnormal condition.

3. A safety shield for use with a laparoscopic electrosurgical apparatus including a trocar cannula having a tubular passage for providing a conduit through a patient's skin to a peritoneal cavity of the patient, the trocar cannula having a proximal end and a distal end and an active electrode probe having a tip and being adapted for connection to an electrosurgical generator and extending through the trocar cannula for effecting at the tip thereof an electrosurgical procedure within the peritoneal cavity, said safety shield comprising
a tubular conductive shield having an inner surface and an outer surface and being removably insertable to an inserted position through the trocar cannula, said shield having a layer of electrical insulation disposed at least over a portion of the outer surface thereof between the trocar cannula and the active probe and where, when the tubular shield is in the inserted position thereof, the shield surrounds, and is electrically insulated from, the active probe from at least (a) a proximal point prior to the proximal end of the trocar cannula to (b) a distal point distal to the distal end of the trocar cannula and in proximity to the tip of the active probe; and an electrical terminal connected to the shield and adapted for connecting the shield to a reference potential;

whereby any current which flows in said shield from said active probe is conducted to said reference potential to thus lessen a risk of patient injury due to an abnormal condition.

4. A shield as in claim 3 including a layer of electrical insulation disposed on at least a portion of the inner surface of the tubular shield.

5. Laparoscopic electrosurgical apparatus comprising:

a trocar cannula having a tubular passage for providing a conduit through a patient's skin to a peritoneal cavity of the patient, the trocar cannula having a proximal end and a distal end;

a tubular conductive shield having an inner surface and an outer surface and being removably insertable to an inserted position through the trocar cannula conduit, said shield having a layer of electrical insulation disposed at least over a portion of the outer surface thereof;

an active electrode probe having a tip and being adapted for connection to an electrosurgical generator and extending through the tubular conductive shield for effecting at the tip thereof an electrosurgical procedure within the peritoneal cavity where, when the tubular shield is in the inserted position thereof, the shield surrounds the active probe from at least (a) a proximal point prior to the proximal end of the trocar cannula to (b) a distal point distal to the distal end of the trocar cannula and in proximity to the tip of the active probe;

at least one layer of electrical insulation disposed between the active probe and the tubular shield; and an electrical terminal connected to the shield and adapted for connecting the shield to a reference potential;

whereby any current which flows in said shield from said active probe is conducted to said reference potential to thus lessen a risk of patient injury due to an abnormal condition.

6. A safety shield for use with an electrosurgical apparatus including a trocar cannula having a tubular passage for providing a conduit through a patient's skin where the trocar cannula has a proximal end and a distal end and an active electrode probe having a tip and being adapted for connection to an electrosurgical generator and extending through the trocar sheath for effecting at the tip thereof an electrosurgical procedure, said safety shield comprising a tubular conductive shield having an inner surface and an outer surface and being removably insertable to an inserted position through the trocar cannula, said shield having a layer of electrical insulation disposed at least over a portion of the outer surface thereof between the trocar cannula and the active probe where, when the tubular shield is in the inserted position thereof, the shield surrounds, and is electrically insulated from, the active probe from at least (a) a proximal point prior to the proximal end of the trocar cannula to (b) a distal point distal to the distal end of the trocar cannula and in proximity to the tip of the active probe; and an electrical terminal disposed on the shield and adapted for connecting the shield to a reference potential;

whereby any current which flows in said shield from said active probe is conducted to said reference potential to thus lessen a risk of patient injury due to an abnormal condition.

7. A shield as in claim 6 including a layer of electrical insulation disposed on at least a portion of the inner surface of the tubular shield.

8. Laparoscopic electrosurgical apparatus comprising:

a trocar cannula having a tubular passage for providing a conduit through a patient's skin to a peritoneal cavity of the patient, the trocar cannula having a proximal end and a distal end;

an elongated insulative member removably insertable through the trocar cannula conduit to an inserted position;

an active electrode having a tip and being attached to the elongated insulative member for effecting at the tip of the electrode an electrosurgical procedure within the peritoneal cavity and including an electrical conductor extending through the elongated member so that the active electrode may be connected to an electrosurgical generator;

a tubular conductive shield extending through the elongated insulative member where, when the elongated insulative member is in the inserted position thereof, the shield surrounds and is electrically insulated from the electrical conductor from at least (a) a point prior to the proximal end of the trocar cannula to (b) a point distal to the distal end of the trocar cannula and in proximity to the tip of the active electrode; and an electrical terminal connected to the shield and adapted for connecting the shield to a reference potential;

whereby any current which flows in said shield from said electrical conductor is conducted to said reference potential to thus lessen a risk of patient injury due to an abnormal condition.

9. Apparatus as in claim 8 where said elongated insulative member includes a passageway extending therethrough.

10. An electrosurgical apparatus comprising:

a trocar cannula having a tubular passage for providing a conduit through a patient's skin, the trocar cannula having a proximal end and a distal end;

an elongated insulative member removably insertable through the trocar cannula conduit to an inserted position;

an active electrode having a tip and being attached to the elongated insulative member for effecting at the tip of the electrode an electrosurgical procedure and including an electrical conductor extending through the elongated member so that the active electrode may be connected to an electrosurgical generator;

a tubular conductive shield extending through the elongated member where, when the elongated insulative member is in the inserted position thereof, the shield surrounds and is electrically insulated from the electrical conductor from at least (a) a point prior to the proximal end of the trocar cannula to (b) a point distal to the distal end of the trocar cannula and in proximity to the tip of the active electrode; and an electrical terminal connected to the shield and adapted for connecting the shield to a reference potential;

whereby any current which flows in said shield from said electrical conductor is conducted to said reference potential to thus lessen a risk of patient injury due to an abnormal condition.

11. Apparatus as in claim 10 where said elongated insulative member includes a passageway extending therethrough.

12. Electrosurgical apparatus comprising:
a handpiece having a tubular passage extending therethrough, the handpiece having a proximal end and a distal end;
an elongated insulative member extending through the handpiece passage;
an active electrode having a tip and being attached to the insulative member for effecting at the tip thereof an electrosurgical procedure and including an electrical conductor extending through the insulative member so that the active electrode may be connected to an electrosurgical generator;
a tubular conductive shield extending through the insulative member and surrounding and being electrically insulated from the electrical conductor from at least (a) a point prior to the proximal end of the handpiece to (b) a point distal to the distal end of the handpiece and in proximity to the tip of the active electrode; and
an electrical terminal connected to the shield and adapted for connecting the shield to a reference potential;
whereby any current which flows in said shield from said electrical conductor is conducted to said reference potential to thus lessen a risk of patient injury due to an abnormal condition.

13. Apparatus as in claim 12 where said elongated insulative member includes a passageway extending therethrough.

14. Apparatus as in claims 5, 2, or 1 where said one layer of insulation is disposed on said active probe.

15. Apparatus as in claims 5, 2, or 1 where said one layer of insulation is disposed on the inner surface of said shield.

16. Apparatus as in claims 5, 2, or 1 including at least two layers of insulation disposed between the active probe and the shield where a first one of the layers is disposed on the active probe and a second one of the layers is disposed on the inner surface of the shield.

17. Apparatus as in claims 5, 2, 3, or 6 where at least said layer of electrical insulation on the outer surface of the tubular conductive shield extends beyond the distal end of the shield and where the extended portion that extends beyond the distal end of the shield has a reduced internal diameter so that the extended portion closely engages the active electrode.

18. Apparatus as in claims 5, 2, 3, 6, or 1 where said active electrode probe is removably insertable through the tubular conductive shield.

19. Apparatus as in claims 3, 8, 10, or 12 where said electrosurgical generator includes a return lead and where said reference potential is at the return lead of the electrosurgical generator.

20. Apparatus as in claim 5, 2, 3, 6, 1, 8, or 12 including alarm means responsive to the monitor circuitry to provide an indication of said abnormal condition.

21. Apparatus as in claim 5, 2, 3, 6, 1, 8 or 12 including means responsive to the monitor circuitry for deactivating the electrosurgical generator in response to said abnormal condition being detected.

22. Apparatus as in claim 5, 2, 3, 6, 1, 8 or 12 where said monitor circuitry includes circuitry for determining whether the amplitude of the shield current exceeds a predetermined threshold.

23. Apparatus as in claim 5, 2, 3, 6, 1, 8 or 12 where said monitor circuitry includes circuitry for determining whether the ratio of the shield current to the current in the return lead to the electrosurgical generator exceeds a predetermined threshold.

24. Apparatus as in claim 5, 2, 3, 6, 1, 8 or 12 including a shield-to-ground detection means for detecting whether the return electrode is connected to the electrosurgical generator including means for detecting whether the voltage on the tubular shield exceeds a predetermined threshold.

25. Apparatus as in claims 5, 2, 3, 6, 1, 8, 10 or 12 including means for latching the tubular conductive shield with respect to the active electrode to thereby provide the capability of adjusting the position of the distal end of the tubular conductive shield with respect to the distal end of the active electrode.

26. Apparatus as in claim 5, 2, 3, 6, 1, 8, or 12 where said monitor circuitry includes circuitry for determining whether a predetermined phase relationship exists between the shield current and the voltage applied to the active lead of the electrosurgical generator.

27. Apparatus as in claim 26 where said predetermined phase relationship is a substantially in phase relationship corresponding to said abnormal condition.

28. Apparatus as in claim 5, 2, 3, 6, 1, 8 or 12 where said monitor circuitry includes spectral sensing circuitry responsive to at least one preselected frequency bandwidth of the shield current.

29. Apparatus as in claim 28 where said spectral sensing circuitry determines whether the amplitude of the electrical energy within said bandwidth exceeds a predetermined threshold.

30. Apparatus as in claim 28 where said frequency bandwidth is below the operating frequency of the electrosurgical generator.

31. Apparatus as in claim 30 where said bandwidth extends from about 50-250 KHz.

32. Apparatus as in claim 5, 2, 3, 6, 1, 8, or 12 where said electrosurgical generator is disposed within a housing.

33. Apparatus as in claim 32 where said monitor circuitry is disposed within said housing.

34. Apparatus as in claim 32 where said monitor circuitry is disposed outside said housing.

35. Apparatus as in claim 34 including means for battery powering the monitor circuitry.

36. Apparatus as in claim 35 where said battery powering means includes means responsive to the flow of current in the shield to provide the battery power.

37. Apparatus as in claim 34 including adaptor means for connecting the monitor circuitry and the return electrode to the return terminal of the electrosurgical generator.

38. Apparatus as in claim 37 where said adaptor means includes sensing means for sensing whether a return electrode has been connected thereto and said monitor circuitry includes means responsive to the sensing means for at least providing an alert in response to the return electrode not being connected to the adaptor.

39. Apparatus as in claim 37 where said adaptor means includes sensing means for sensing whether the adaptor has been connected to the electrosurgical generator and said monitor circuitry includes means responsive to the sensing means for at least providing an alert in response to the adaptor not being connected to the generator.

40. Apparatus as in claim 5, 2, 3, 6, 1, 8 or 12 where said monitor circuitry includes circuitry for determining whether a predetermined amount of shield current is present subsequent to the activation of the electrosurgical generator.

41. Apparatus as in claim 40 including means responsive to voltage applied to the active lead of the generator to sense said activation of the generator.

42. Apparatus as in claim 40 including means responsive to the current in the return lead to the generator to sense said activation of the generator.

* * * * *

UNITED STATES PATENT AND TRADEMARK OFFICE
CERTIFICATE OF CORRECTION

PATENT NO. : 5,312,401
DATED : May 17, 1994
INVENTOR(S) : David W. NEWTON et al.

It is certified that error appears in the above-indentified patent and that said Letters Patent is hereby corrected as shown below:

Column 17, line 50, cancel beginning with "1. An electrosurgical apparatus comprising:" to and including "injury due to an abnormal condition." in column 19, line 7, and insert the following claims:

--1. An electrosurgical apparatus for use with an electrosurgical generator comprising:

a handpiece having a tubular passage extending therethrough, the handpiece having a proximal end and a distal end;

a tubular conductive shield having an inner surface and an outer surface and being removably insertable through the handpiece passage to an inserted position, said shield having a layer of electrical insulation disposed at least over the outer surface thereof;

an active electrode probe having a tip and being adapted for connection to said electrosurgical generator and extending through the tubular conductive shield for effecting at the tip thereof an electrosurgical procedure where, when the tubular shield is in the inserted position thereof, the shield surrounds the active probe from at least (a) a proximal point prior to the proximal end of the handpiece to (b) a distal point distal to the distal end of the handpiece and in proximity to the tip of the active probe;

at least one layer of electrical insulation disposed between the active probe and the tubular shield;

UNITED STATES PATENT AND TRADEMARK OFFICE
CERTIFICATE OF CORRECTION

PATENT NO. : 5,312,401
DATED : May 17, 1994
INVENTOR(S) : David W. NEWTON et al.

It is certified that error appears in the above-indentified patent and that said Letters Patent is hereby corrected as shown below:

an electrical terminal connected to the shield and adapted for connecting the shield to a reference potential;

whereby any current which flows in said shield from said active probe is conducted to said reference potential to thus lessen a risk of patient injury due to an abnormal condition; and monitor circuitry connected between said electrical terminal and said reference potential, said monitor circuitry being responsive to current in the shield to determine whether said abnormal condition exists.

2. An electrosurgical apparatus for use with an electrosurgical generator comprising:

a trocar cannula having a tubular passage for providing a conduit through a patient's skin where the trocar cannula has a proximal end and a distal end;

a tubular conductive shield having an inner surface and an outer surface and being removably insertable to an inserted position through the trocar cannula conduit, said shield having a layer of electrical insulation disposed at least over the outer surface thereof;

an active electrode probe having a tip and being adapted for connection to said electrosurgical generator and extending through the tubular conductive shield for effecting at the tip thereof an electrosurgical procedure within a patient's body where, when the

UNITED STATES PATENT AND TRADEMARK OFFICE
CERTIFICATE OF CORRECTION

PATENT NO. : 5,312,401
DATED : May 17, 1994
INVENTOR(S) : David W. NEWTON et al.

It is certified that error appears in the above-indentified patent and that said Letters Patent is hereby corrected as shown below:

tubular shield is in the inserted position thereof, the shield surrounds and is electrically insulated from the active probe from at least (a) a proximal point prior to the proximal end of the trocar cannula to (b) a distal point distal to the distal end of the trocar cannula and in proximity to the tip of the active probe;

at least one layer of electrical insulation disposed between the active probe and the tubular shield;

an electrical terminal connected to the shield and adapted for connecting the shield to a reference potential;

whereby any current which flows in said shield from said active probe is conducted to said reference potential to thus lessen a risk of patient injury due to an abnormal condition; and monitor circuitry connected between said electrical terminal and said reference potential, said monitor circuitry being responsive to current in the shield to determine whether said abnormal condition exists.

3. A safety shield system for use with a laparoscopic electrosurgical apparatus including a trocar cannula having a tubular passage for providing a conduit through a patient's skin to a peritoneal cavity of the patient, the trocar cannula having a proximal end and a distal end, an electrosurgical generator and an active electrode probe having a tip and being adapted for connection to said electrosurgical generator and extending through the trocar cannula for

UNITED STATES PATENT AND TRADEMARK OFFICE
CERTIFICATE OF CORRECTION

PATENT NO. : 5,312,401
DATED : May 17, 1994
INVENTOR(S) : David W. NEWTON et al.

It is certified that error appears in the above-indentified patent and that said Letters Patent is hereby corrected as shown below:

effecting at the tip thereof an electrosurgical procedure within the peritoneal cavity, said safety shield comprising a tubular conductive shield having an inner surface and an outer surface and being removably insertable to an inserted position through the trocar cannula, said shield having a layer of electrical insulation disposed at least over a portion of the outer surface thereof between the trocar cannula and the active probe and where, when the tubular shield is in the inserted position thereof, the shield surrounds, and is electrically insulated from, the active probe from at least (a) a proximal point prior to the proximal end of the trocar cannula to (b) a distal point distal to the distal end of the trocar cannula and in proximity to the tip of the active probe;

an electrical terminal connected to the shield and adapted for connecting the shield to a reference potential;

whereby any current which flows in said shield from said active probe is conducted to said reference potential to thus lessen a risk of patient injury due to an abnormal condition; and monitor circuitry connected between said electrical terminal and said reference potential, said monitor circuitry being responsive to current in the shield to determine whether said abnormal condition exists.--

UNITED STATES PATENT AND TRADEMARK OFFICE
CERTIFICATE OF CORRECTION

PATENT NO. : 5,312,401

DATED : May 17, 1994

INVENTOR(S) : David W. NEWTON et al.

Page 5 of 12

It is certified that error appears in the above-indentified patent and that said Letters Patent is hereby corrected as shown below:

Column 19, line 11, cancel beginning with "5. Laparoscopic electrosurgical apparatus" to and including "patient injury due to an abnormal condition." in column 20, lines 3 and 4, and insert the following claims:

--5. Laparoscopic electrosurgical apparatus for use with an electrosurgical generator comprising:

a trocar cannula having a tubular passage for providing a conduit through a patient's skin to a peritoneal cavity of the patient, the trocar cannula having a proximal end and a distal end;

a tubular conductive shield having an inner surface and an outer surface and being removably insertable to an inserted position through the trocar cannula conduit, said shield having a layer of electrical insulation disposed at least over a portion of the outer surface thereof;

an active electrode probe having a tip and being adapted for connection to said electrosurgical generator and extending through the tubular conductive shield for effecting at the tip thereof an electrosurgical procedure within the peritoneal cavity where, when the tubular shield is in the inserted position thereof, the shield surrounds the active probe from at least (a) a proximal point prior to the proximal end of the trocar cannula to (b) a distal point distal to the distal end of the trocar cannula and in proximity to the tip of the active probe;

UNITED STATES PATENT AND TRADEMARK OFFICE
CERTIFICATE OF CORRECTION

PATENT NO. : 5,312,401
DATED : May 17, 1994
INVENTOR(S) : David W. NEWTON et al.

It is certified that error appears in the above-identified patent and that said Letters Patent is hereby corrected as shown below:

at least one layer of electrical insulation disposed between the active probe and the tubular shield;

an electrical terminal connected to the shield and adapted for connecting the shield to a reference potential;

whereby any current which flows in said shield from said active probe is conducted to said reference potential to thus lessen a risk of patient injury due to an abnormal condition; and monitor circuitry connected between said electrical terminal and said reference potential, said monitor circuitry being responsive to current in the shield to determine whether said abnormal condition exists.

6. A safety shield system for use with an electrosurgical apparatus including a trocar cannula having a tubular passage for providing a conduit through a patient's skin where the trocar cannula has a proximal end and a distal end, an electrosurgical generator, and an active electrode probe having a tip and being adapted for connection to said electrosurgical generator and extending through the trocar cannula for effecting at the tip thereof an electrosurgical procedure, said safety shield comprising a tubular conductive shield having an inner surface and an outer surface and being removably insertable to an inserted position through the trocar cannula, said shield having a layer of electrical insulation disposed at least over a portion of the outer

UNITED STATES PATENT AND TRADEMARK OFFICE
CERTIFICATE OF CORRECTION

PATENT NO. : 5,312,401
DATED : May 17, 1994
INVENTOR(S) : David W. NEWTON et al.

It is certified that error appears in the above-identified patent and that said Letters Patent is hereby corrected as shown below:

surface thereof between the trocar cannula and the active probe where, when the tubular shield is in the inserted position thereof, the shield surrounds, and is electrically insulated from, the active probe from at least (a) a proximal point prior to the proximal end of the trocar cannula to (b) a distal point distal to the distal end of the trocar cannula and in proximity to the tip of the active probe;

an electrical terminal disposed on the shield and adapted for connecting the shield to a reference potential;

whereby any current which flows in said shield from said active probe is conducted to said reference potential to thus lessen a risk of patient injury due to an abnormal condition; and monitor circuitry connected between said electrical terminal and said reference potential, said monitor circuitry being responsive to current in the shield to determine whether said abnormal condition exists.--

Column 20, line 8, cancel beginning with "8. Laparoscopic electrosurgical apparatus" to and including "patient injury due to an abnormal condition." in column 20, lines 38 and 39, and insert the following claim:

UNITED STATES PATENT AND TRADEMARK OFFICE
CERTIFICATE OF CORRECTION

PATENT NO. : 5,312,401
DATED : May 17, 1994
INVENTOR(S) : David W. NEWTON et al.

It is certified that error appears in the above-identified patent and that said Letters Patent is hereby corrected as shown below:

--8. Laparoscopic electrosurgical apparatus for use with an electrosurgical generator comprising:

a trocar cannula having a tubular passage for providing a conduit through a patient's skin to a peritoneal cavity of the patient, the trocar cannula having a proximal end and a distal end;

an elongated insulative member removably insertable through the trocar cannula conduit to an inserted position;

an active electrode having a tip and being attached to the elongated insulative member for effecting at the tip of the electrode an electrosurgical procedure within the peritoneal cavity and including an electrical conductor extending through the elongated member so that the active electrode may be connected to said electrosurgical generator;

a tubular conductive shield extending through the elongated insulative member where, when the elongated insulative member is in the inserted position thereof, the shield surrounds and is electrically insulated from the electrical conductor from at least (a) a point prior to the proximal end of the trocar cannula to (b) a point distal to the distal end of the trocar cannula and in proximity to the tip of the active electrode; and an electrical terminal connected to the shield and adapted for connecting the shield to a reference potential;

whereby any current which flows in said shield from said electrical conductor is conducted to said reference potential to

UNITED STATES PATENT AND TRADEMARK OFFICE
CERTIFICATE OF CORRECTION

PATENT NO. : 5,312,401
DATED : May 17, 1994
INVENTOR(S) : David W. NEWTON et al.

It is certified that error appears in the above-identified patent and that said Letters Patent is hereby corrected as shown below:

thus lessen a risk of patient injury due to an abnormal condition; and monitor circuitry connected between said electrical terminal and said reference potential, said monitor circuitry being responsive to current in the shield to determine whether said abnormal condition exists.--

Column 20, line 43, cancel beginning with "10. An electrosurgical apparatus comprising:" to and including "patient injury due to an abnormal condition." in column 21, lines 3 and 4, and insert the following claim:

--10. An electrosurgical apparatus for use with an electrosurgical generator comprising:

a trocar cannula having a tubular passage for providing a conduit through a patient's skin, the trocar cannula having a proximal end and a distal end;

an elongated insulative member removably insertable through the trocar cannula conduit to an inserted position;

an active electrode having a tip and being attached to the elongated insulative member for effecting at the tip of the electrode an electrosurgical procedure and including an electrical conductor extending through the elongated member so that the active electrode may be connected to said electrosurgical generator;

UNITED STATES PATENT AND TRADEMARK OFFICE
CERTIFICATE OF CORRECTION

| | | |
|---|---|---|
| PATENT NO. : | 5,312,401 | Page 10 of 12 |
| DATED : | May 17, 1994 | |
| INVENTOR(S) : | David W. NEWTON et al. | |

It is certified that error appears in the above-identified patent and that said Letters Patent is hereby corrected as shown below:

a tubular conductive shield extending through the elongated member where, when the elongated insulative member is in the inserted position thereof, the shield surrounds and is electrically insulated from the electrical conductor from at least (a) a point prior to the proximal end of the trocar cannula to (b) a point distal to the distal end of the trocar cannula and in proximity to the tip of the active electrode;

an electrical terminal connected to the shield and adapted for connecting the shield to a reference potential;

whereby any current which flows in said shield from said electrical conductor is conducted to said reference potential to thus lessen a risk of patient injury due to an abnormal condition; and monitor circuitry connected between said electrical terminal and said reference potential, said monitor circuitry being responsive to current in the shield to determine whether said abnormal condition exists.--

Column 21, line 8, cancel beginning with "12. Electrosurgical apparatus comprising:" to and including "patient injury to an abnormal condition." in column 21, lines 33 and 34, and insert the following claim:

--12. Electrosurgical apparatus for use with an electrosurgical generator comprising:

UNITED STATES PATENT AND TRADEMARK OFFICE
CERTIFICATE OF CORRECTION

| | | |
|---|---|---|
| PATENT NO. : | 5,312,401 | |
| DATED : | May 17, 1994 | |
| INVENTOR(S) : | David W. NEWTON et al. | |

It is certified that error appears in the above-identified patent and that said Letters Patent is hereby corrected as shown below:

a handpiece having a tubular passage extending therethrough, the handpiece having a proximal end and a distal end;

an elongated insulative member extending through the handpiece passage;

an active electrode having a tip and being attached to the insulative member for effecting at the tip thereof an electrosurgical procedure and including an electrical conductor extending through the insulative member so that the active electrode may be connected to said electrosurgical generator;

a tubular conductive shield extending through the insulative member and surrounding and being electrically insulated from the electrical conductor from at least (a) a point prior to the proximal end of the handpiece to (b) a point distal to the distal end of the handpiece and in proximity to the tip of the active electrode;

an electrical terminal connected to the shield and adapted for connecting the shield to a reference potential;

UNITED STATES PATENT AND TRADEMARK OFFICE
CERTIFICATE OF CORRECTION

PATENT NO. : 5,312,401
DATED : May 17, 1994
INVENTOR(S) : David W. NEWTON et al.

It is certified that error appears in the above-identified patent and that said Letters Patent is hereby corrected as shown below:

whereby any current which flows in said shield from said electrical conductor is conducted to said reference potential to thus lessen a risk of patient injury due to an abnormal condition; and monitor circuitry connected between said electrical terminal and said reference potential, said monitor circuitry being responsive to current in the shield to determine whether said abnormal condition exists.--

Signed and Sealed this

Twenty-fifth Day of July, 2000

Attest:

Q. TODD DICKINSON

*Attesting Officer*    *Director of Patents and Trademarks*